(12) United States Patent
Wang et al.

(10) Patent No.: US 11,284,792 B2
(45) Date of Patent: Mar. 29, 2022

(54) METHODS AND SYSTEMS FOR ENHANCING MICROANGIOGRAPHY IMAGE QUALITY

(71) Applicant: UNIVERSITY OF WASHINGTON, Seattle, WA (US)

(72) Inventors: Ruikang K. Wang, Seattle, WA (US); Anqi Zhang, Seattle, WA (US); Qinqin Zhang, Seattle, WA (US)

(73) Assignee: University of Washington, Seattle, WA (US)

( * ) Notice: Subject to any disclaimer, the term of this patent is extended or adjusted under 35 U.S.C. 154(b) by 1240 days.

(21) Appl. No.: 15/552,437

(22) PCT Filed: Mar. 7, 2016

(86) PCT No.: PCT/US2016/021138
§ 371 (c)(1),
(2) Date: Aug. 21, 2017

(87) PCT Pub. No.: WO2016/144854
PCT Pub. Date: Sep. 15, 2016

(65) Prior Publication Data
US 2018/0042473 A1 Feb. 15, 2018

Related U.S. Application Data

(60) Provisional application No. 62/129,410, filed on Mar. 6, 2015.

(51) Int. Cl.
*A61B 5/00* (2006.01)
*A61B 3/10* (2006.01)
(Continued)

(52) U.S. Cl.
CPC ............ *A61B 3/102* (2013.01); *A61B 3/0025* (2013.01); *A61B 3/1241* (2013.01); *A61B 3/14* (2013.01);
(Continued)

(58) Field of Classification Search
CPC ... A61B 2576/02; A61B 3/0025; A61B 3/102; A61B 3/1241; A61B 3/14; A61B 5/0066;
(Continued)

(56) References Cited

U.S. PATENT DOCUMENTS 7,995,814 B2    8/2011   Fingler et al.
8,345,945 B2    1/2013   Song et al.
(Continued)

FOREIGN PATENT DOCUMENTS

WO    2013/116689 A1    8/2013

OTHER PUBLICATIONS

An, et al., "High-resolution wide-field imaging of retinal and choroidal blood perfusion with optical microangiography," J. Biomed. Opt. 15(2), 026011 (2010).
(Continued)

*Primary Examiner* — Mark D Remaly
(74) *Attorney, Agent, or Firm* — McDonnell Boehnen Hulbert & Berghoff LLP

(57) ABSTRACT

Systems and methods for enhancing quality of a flow image of a sample of a subject are provided. The method comprises acquiring a first flow image from a plurality of first OMAG scans of the sample, and acquiring a structure image from a second OMAG scan of the sample. Data based on pixel intensity values from the flow image and pixel intensity values from the structure image are then plotted onto a graph and from the graph, may be differentiated into a first data group representing static structure signals and a second data group representing flow signals. The method then includes
(Continued)

suppressing pixels in the flow image corresponding to the first data group. The flow signal may also be multiplied by a weighting factor to suppress artifacts in the image.

18 Claims, 14 Drawing Sheets

(51) Int. Cl.
| | |
|---|---|
| A61B 5/026 | (2006.01) |
| A61B 3/00 | (2006.01) |
| A61B 3/12 | (2006.01) |
| A61B 3/14 | (2006.01) |
| G06T 5/00 | (2006.01) |

(52) U.S. Cl.
CPC .......... *A61B 5/0066* (2013.01); *A61B 5/0261* (2013.01); *G06T 5/005* (2013.01); *A61B 5/489* (2013.01); *A61B 2576/02* (2013.01); *G06T 2207/10101* (2013.01); *G06T 2207/20072* (2013.01); *G06T 2207/20076* (2013.01)

(58) Field of Classification Search
CPC .................. A61B 5/0261; A61B 5/489; G06T 2207/10101; G06T 2207/20072; G06T 2207/20076; G06T 5/005
See application file for complete search history.

(56) References Cited

U.S. PATENT DOCUMENTS

| | | | |
|---|---|---|---|
| 8,433,393 | B2 | 4/2013 | Sharma et al. |
| 9,107,609 | B2 | 8/2015 | Sharma et al. |
| 2008/0025570 | A1 | 1/2008 | Fingler et al. |
| 2012/0307014 | A1 | 12/2012 | Wang |
| 2013/0301000 | A1 | 11/2013 | Sharma et al. |
| 2014/0073917 | A1 | 3/2014 | Huang et al. |
| 2014/0221827 | A1 | 8/2014 | Motaghiannezam et al. |
| 2014/0228681 | A1* | 8/2014 | Jia ...................... G01B 9/02045 600/425 |

OTHER PUBLICATIONS

An, et al., "Ultrahigh sensitive optical microangiography for in vivo imaging of microcirculations within human skin tissue beds," Opt. Express 18(8), 8220-8228 (2010).
An, et al., "Using ultrahigh sensitive optical microangiography to achieve comprehensive depth resolved microvasculature mapping for human retina," J. Biomed. Opt. 16(10), 106013 (2011).
Baillif, et al., "Retinal fluorescein and indocyanine green angiography and spectral-domain optical coherence tomography findings in acute retinal pigment epitheliitis," Retina 31(6), 1156-1163 (2011).
Baran and Wang, "Capillary blood flow imaging within human finger cuticle using optical microangiography," J. Biophotonics, 8, 46-51 (2015).
Barton and Stromski, "Flow measurement without phase information in optical coherence tomography images," Opt. Express 13(14), 5234-5239 (2005).
Baumuller, et al., "Outer retinal hyperreflective spots on spectral-domain optical coherence tomography in macular telangiectasia type 2," Ophthalmology 117(11), 2162-2168 (2010).
Bek, "Regional morphology and pathophysiology of retinal vascular disease," Prog. Retin. Eye Res. 36, 247-259 (2013).
Blatter, et al., "Ultrahigh-speed non-invasive widefield angiography," J. Biomed. Opt. 17(7), 070505 (2012).
Bolz, et al. Diabetic Retinopathy Research Group Vienna, "Optical coherence tomographic hyperreflective foci: a morphologic sign of lipid extravasation in diabetic macular edema," Ophthalmology 116(5), 914-920 (2009).
Braaf, et al., "Angiography of the retina and the choroid with phase-resolved OCT using interval-optimized backstitched B-scans," Opt. Express 20(18), 20516-20534 (2012).
Chen, et al., "Noninvasive imaging of in vivo blood flow velocity using optical Doppler tomography," Opt. Lett. 22(14), 1119-1121 (1997).
Choi, et al., "Improved microcirculation imaging of human skin in vivo using optical microangiography with a correlation mapping mask," J. Biomed. Opt. 19(3), 036010 (2014).
Coscas, et al., "Hyperreflective dots: a new spectral-domain optical coherence tomography entity for follow-up and prognosis in exudative age-related macular degeneration," Ophthalmologica 229(1), 32-37 (2013).
Deak, et al., "Effect of retinal photocoagulation on intraretinal lipid exudates in diabetic macular edema documented by optical coherence tomography," Ophthalmology 117(4), 773-779 (2010).
Enfield, et al., "In vivo imaging of the microcirculation of the volar forearm using correlation mapping optical coherence tomography (cmOCT)," Biomed. Opt. Express 2(5), 1184-1193 (2011).
Fingler, et al., "Mobility and transverse flow visualization using phase variance contrast with spectral domain optical coherence tomography," Opt. Express 15(20), 12636-12653 (2007).
Fingler, et al., "Volumetric microvascular imaging of human retina using optical coherence tomography with a novel motion contrast technique," Opt. Express 17(24), 22190-22200 (2009).
Fujimoto, J.G., et al., Optical Coherence Tomography: An Emerging Technology for Biomedical Imaging and Optical Biopsy, Neoplasia, (2000) 2(1-2): 9-25.
Wang, et al., "Optical microangiography provides depth-resolved images of directional ocular blood perfusion in posterioreye segment," J. Biomed Opt. 15(2), 020502 (2010).
Huang, et al., "Efficient method to suppress artifacts caused by tissue hyper-reflections in optical microangiography of retina in vivo," Biomed Opt. Express 6(4), 1195-1208 (2015).
Huang, et al., "Swept-source OCT angiography of the retinal vasculature using intensity differentiation based OMAG algorithms," OSLI Retina. 45(5), 382-389 (2014).
Jia, et al. "Split-spectrum amplitude-decorrelation angiography with optical coherence tomography," Opt. Express 20(4), 4710-4725 (2012).
Jia, et al., "Optical microangiography provides an ability to monitor responses of cerebral microcirculation to hypoxia and hyperoxia in mice," J. Biomed. Opt. 16(9), 096019 (2011).
Jia, Y et al. "Quantitative optical coherence tomography angiography of choroidal neovascularization in age-related macular degeneration" Ophthalmology, vol. 121, No. 7, Jul. 2014.
Keane and Sadda, "Imaging chorioretinal vascular disease," Eye (Lond.) 24(3), 422-427 (2009).
Kim, et al., "Optical imaging of the chorioretinal vasculature in the living human eye," Proc. Natl. Acad. Sci. U.S.A. 110(35), 14354-14359 (2013).
Leitgeb, et al., "Real-time assessment of retinal blood flow with ultrafast acquisition by color Doppler Fourier domain optical coherence tomography," Opt. Express 11(23), 3116-3121 (2003).
Leitgeb, R.A., et al., Doppler Optical Coherence Tomography, Progress in Retinal and Eye Research, (2014) 41(100): 26-43.
Li, et al., "Application of Thinned-Skull Cranial Window to Mouse Cerebral Blood Flow Imaging Using Optical Microangiography," PLoS ONE 9(11), e113658 (2014).
Liu, X et al. "Motion analysis and removal in intensity variation based OCT angiography" Biomedical Optics Express, vol. 5, No. 11, Oct. 7, 2014.
Mariampillai, et al., "Speckle variance detection of microvasculature using swept-source optical coherence tomography," Opt. Lett. 33(13), 1530-1532 (2008).
Mendis, et al., "Correlation of histologic and clinical images to determine the diagnostic value of fluorescein angiography for studying retinal capillary detail," Invest Ophthalmol Vis. Sci. 51(11), 5864-5869 (2010).
Motaghiannezam and Fraser, "Logarithmic intensity and speckle-based motion contrast methods for human retinal vasculature visualization using swept source optical coherence tomography," Biomed. Opt. Express 3(3), 503-521 (2012).

(56) References Cited

OTHER PUBLICATIONS

Popovic, et al., "Noninvasive imaging of human foveal capillary network using dual-conjugate adaptive optics," Invest. Ophthalmol. Vis. Sci. 52(5), 2649-2655 (2011).
Rasmussen and Williams, Gaussian Processes for Machine Learning (the MIT Press, 2006).
Schmitt, et al., "Speckle in optical coherence tomography," J. Biomed. Opt. 4(1), 95-105 (1999).
Singh, et al., "Segmentation of Doppler optical coherence tomography signatures using a support-vector machine," Biomed. Opt. Express 2(5), 1328-1339 (2011).
Srinivasan, et al., "Rapid volumetric angiography of cortical microvasculature with optical coherence tomography," Opt. Lett. 35(1), 43-45 (2010).
Tam, et al., "Disruption of the retinal parafoveal capillary network in type 2 diabetes before the onset of diabetic retinopathy," Invest. Ophthalmol. Vis. Sci. 52(12), 9257-9266 (2011).
Thomas, D., et al., Optical Coherence Tomography—A Review of the Principles and Contemporary Uses in Retinal Investigation, Eye, (2004) 18: 561-570.
Thorell, et al., "Swept-source OCT angiography of macular telangiectasia type 2," Ophthalmic Surg Lasers Imaging Retina 45(5), 369-380 (2014).
Uji, et al., "Association between hyperreflective foci in the outer retina, status of photoreceptor layer, and visual acuity in diabetic macular edema," Am. J. Ophthalmol. 153(4), 710-717 (2012).
Vakoc, et al., "Cancer imaging by optical coherence tomography: preclinical progress and clinical potential," Nat. Rev. Cancer 12(5), 363-368 (2012).
Wagnieres, et al., "An optical phantom with tissue-like properties in the visible for use in PDT and fluorescence spectroscopy," Phys. Med. Biol. 42(7), 1415-1426 (1997).
Wang and An, "Doppler optical micro-angiography for volumetric imaging of vascular perfusion in vivo," Opt. Express 17(11), 8926-8940 (2009).
Wang and Ma, "Real-time flow imaging by removing texture pattern artifacts in spectral-domain optical Doppler tomography," Opt. Lett. 31(20), 3001-3003 (2006).
Wang and Wang, "Autocorrelation optical coherence tomography for mapping transverse particle-flow velocity," Opt. Lett. 35(21), 3538-3540 (2010).
Wang, et al., "Depth-resolved imaging of capillary networks in retina and choroid using ultrahigh sensitive optical microangiography," Opt. Lett. 35(9), 1467-1469 (2010).
The International Search Report (ISR) with Written Opinion for PCT/US2016/021138 dated May 20, 2016, pp. 1-11.

Jia, Yali et al. "Quantitative optical coherence tomography angiography of choroidal neovascularization in age-related macular degeneration" Ophthalmology (2014) vol. 121(7), pp. 1435-1444.
Wang, Ruikang K. et al. "Doppler optical micro-angiography for volumetric imaging of vascular perfusion in vivo" Optics Express (2009) vol. 17(11), pp. 8926-8940.
Zhang, Anqi et al. "Feature space optical coherence tomography based micro-angiography" Biomedical Optics Express (2015) vol. 6(5), pp. 1919-1928.
Liu, Xuan et al. "Motion analysis and removal in intensity variation based OCT angiography" Biomedical Optics Express (2014) vol. 5(11), pp. 3833-3847.
Wang, et al., "Three dimensional optical angiography," Opt. Express 15(7), 4083-4097 (2007).
White, et al., "In vivo dynamic human retinal blood flow imaging using ultra-high-speed spectral domain optical coherence tomography," Opt. Express 11(25), 3490-3497 (2003).
Yasuno, et al., "In vivo high-contrast imaging of deep posterior eye by 1-μm swept source optical coherence tomography and scattering optical coherence angiography," Opt Express 15(10), 6121-6139 (2007).
Yi, et al., "In Vivo Functional Microangiography by Visible-Light Optical Coherence Tomography" Biomedical Optics Express (2014) vol. 5 / Issue 10 / p. 3603-3612.
Yin, et al., "User-guided segmentation for volumetric retinal optical coherence tomography images," J. Biomed. Opt. 19(8), 086020 (2014).
Yu and Chen, "Doppler variance imaging for three-dimensional retina and choroid angiography," J. Biomed. Opt. 15(1), 016029 (2010).
Zhang, A et al. "Feature space optical coherence tomography based micro-angiography" Biomedical Optics Express, vol. 6, No. 5, Apr. 28, 2015.
Zhang, et al., "Multifunctional 1050 nm spectral domain OCT system at 147kHz for posterior eye imaging," Mod. Technol. Med. 7(1), 7-12 (2015).
Zhang, et al.,"Generic pixel-wise speckle detection in Fourier-domain optical coherence tomography images," Opt. Lett. 39(15), 4392-4395 (2014).
Zhi, et al., "Supercontinuum light source enables in vivo optical microangiography of capillary vessels within tissue beds," Opt. Lett. 36(16), 3169-3171 (2011).
Zhi, et al., "Volumetric and quantitative imaging of retinal blood flow in rats with optical microangiography," Biomed. Opt. Express 2(3), 579-591 (2011).

\* cited by examiner

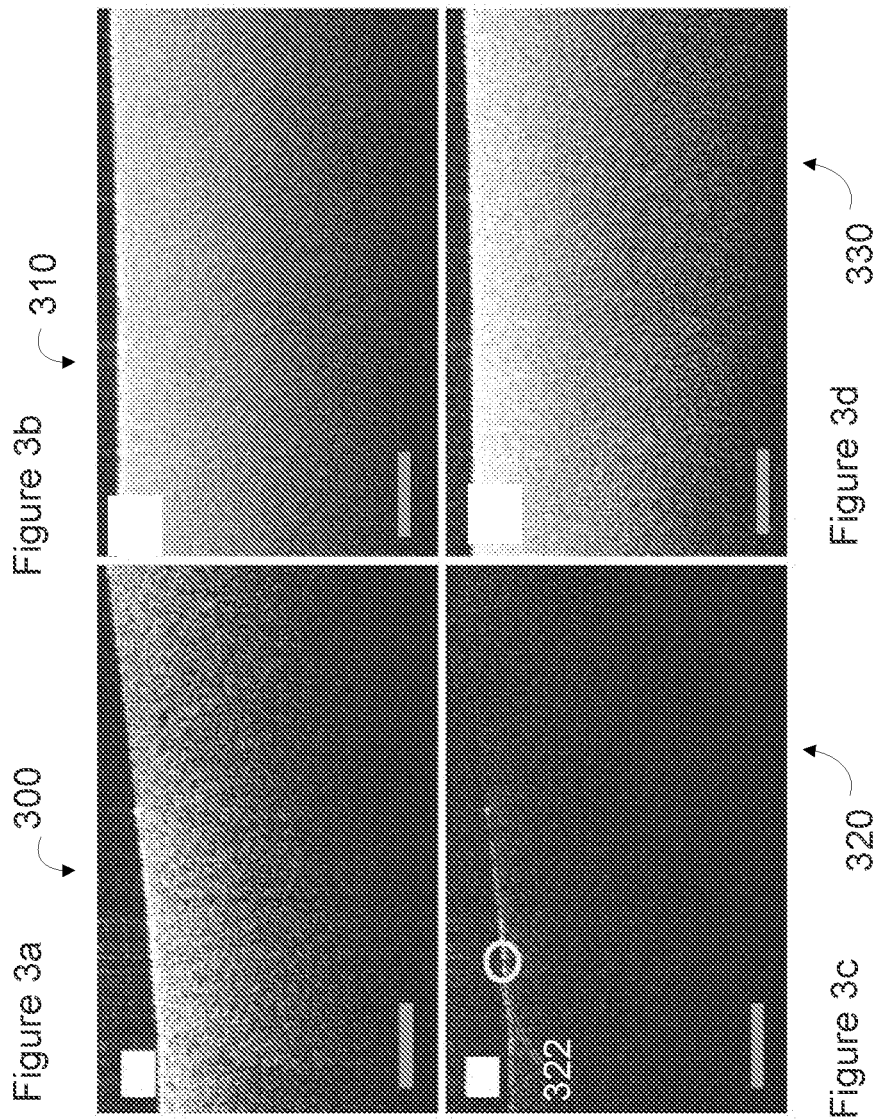

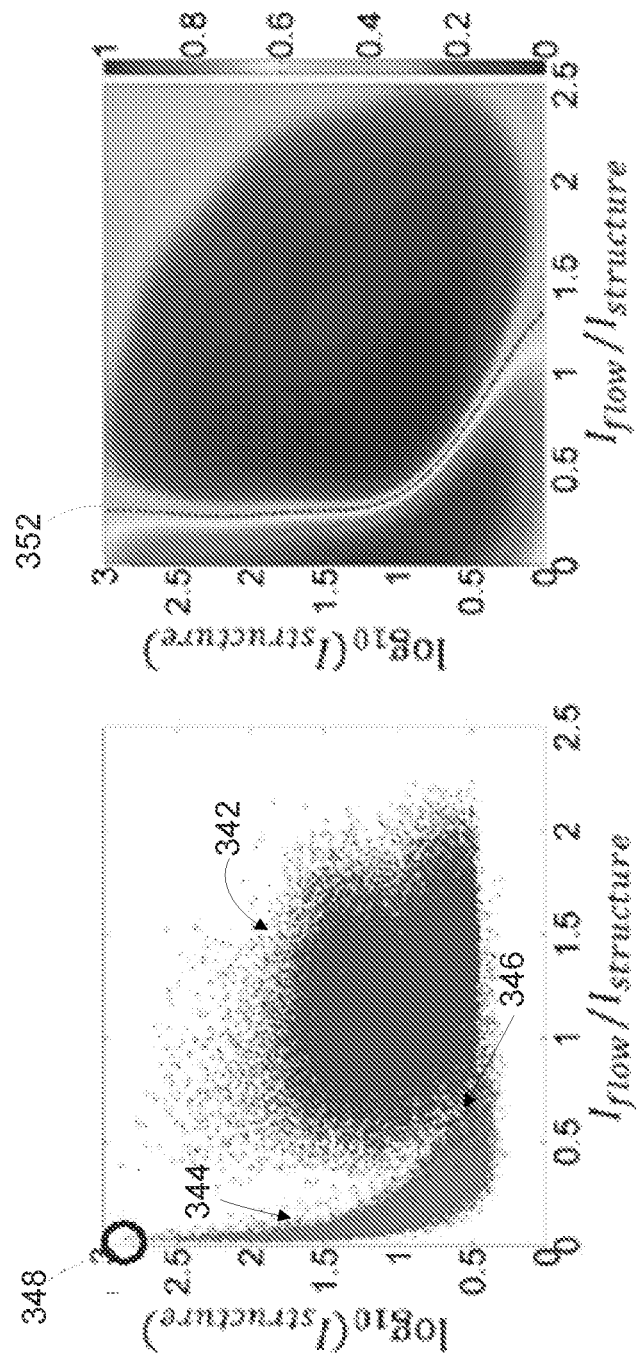

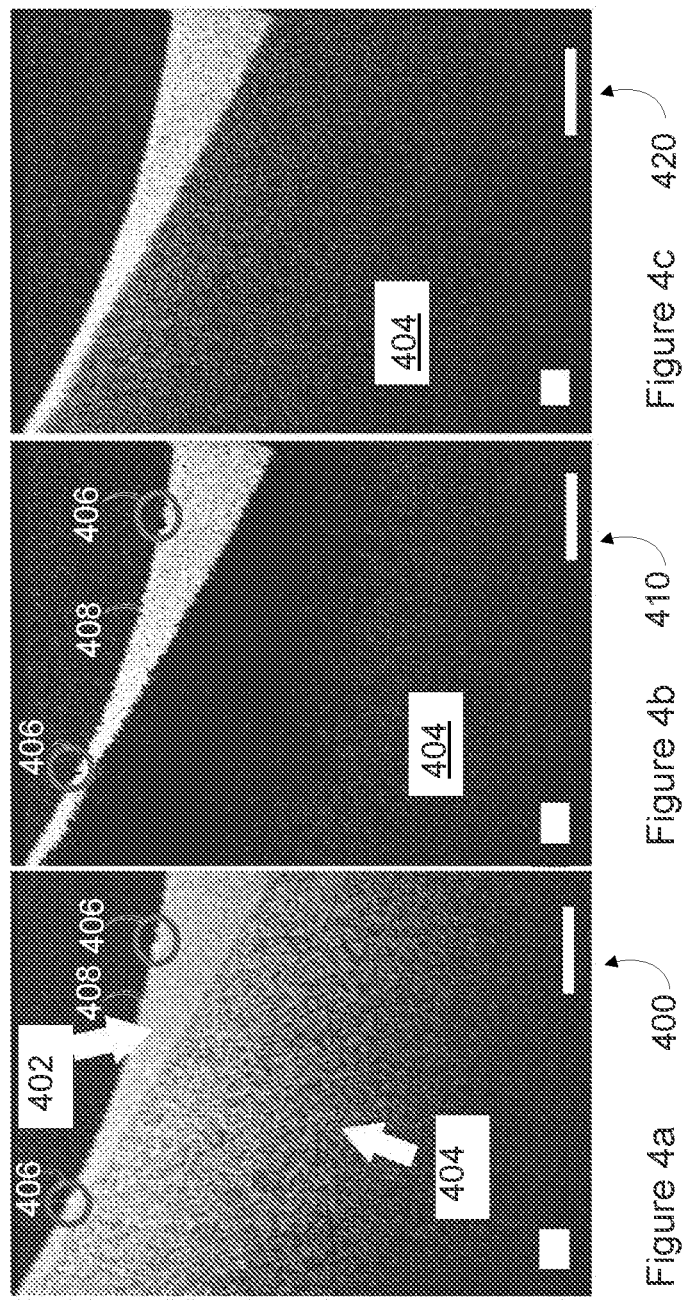
Figure 4a 400   Figure 4b 410   Figure 4c 420

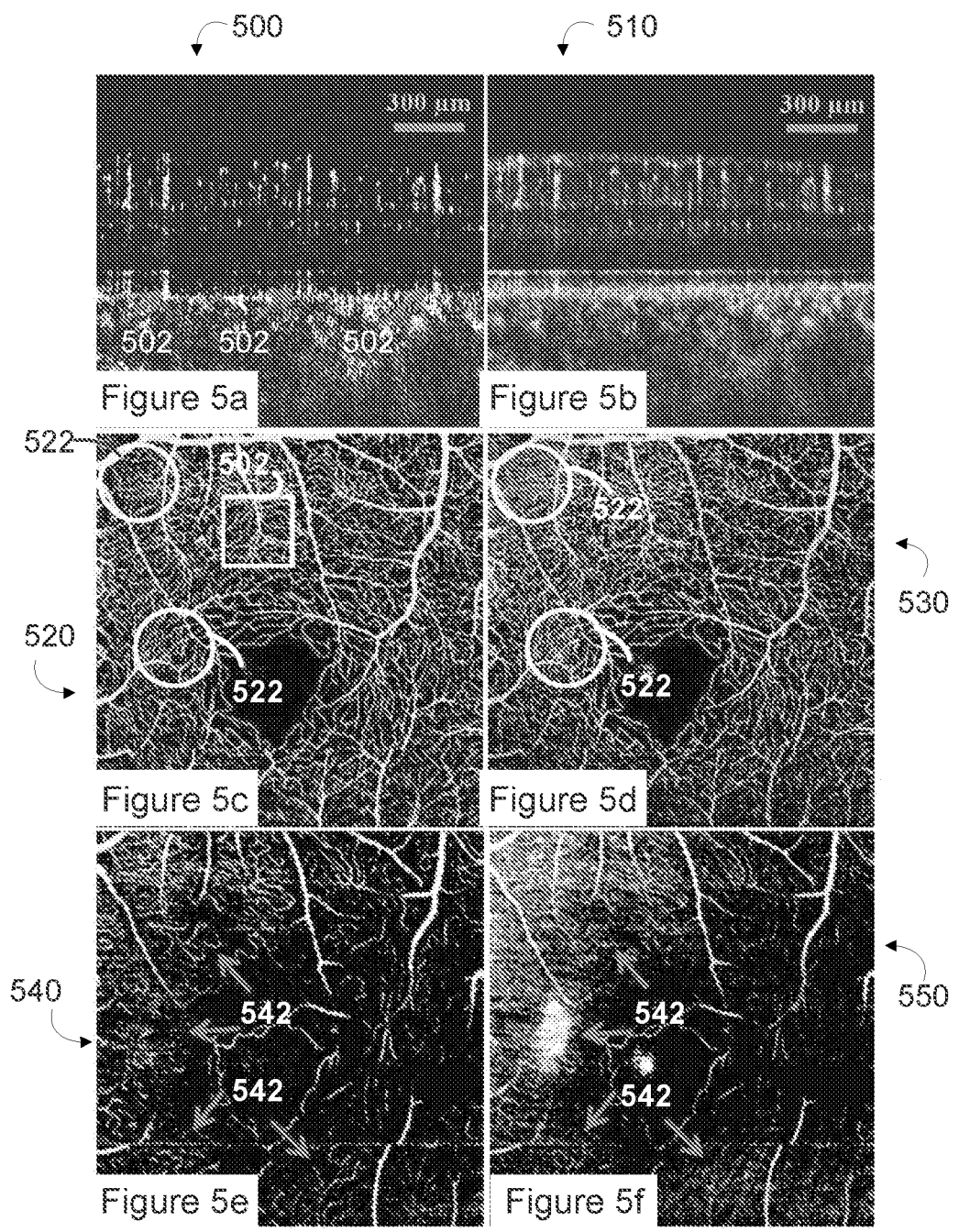

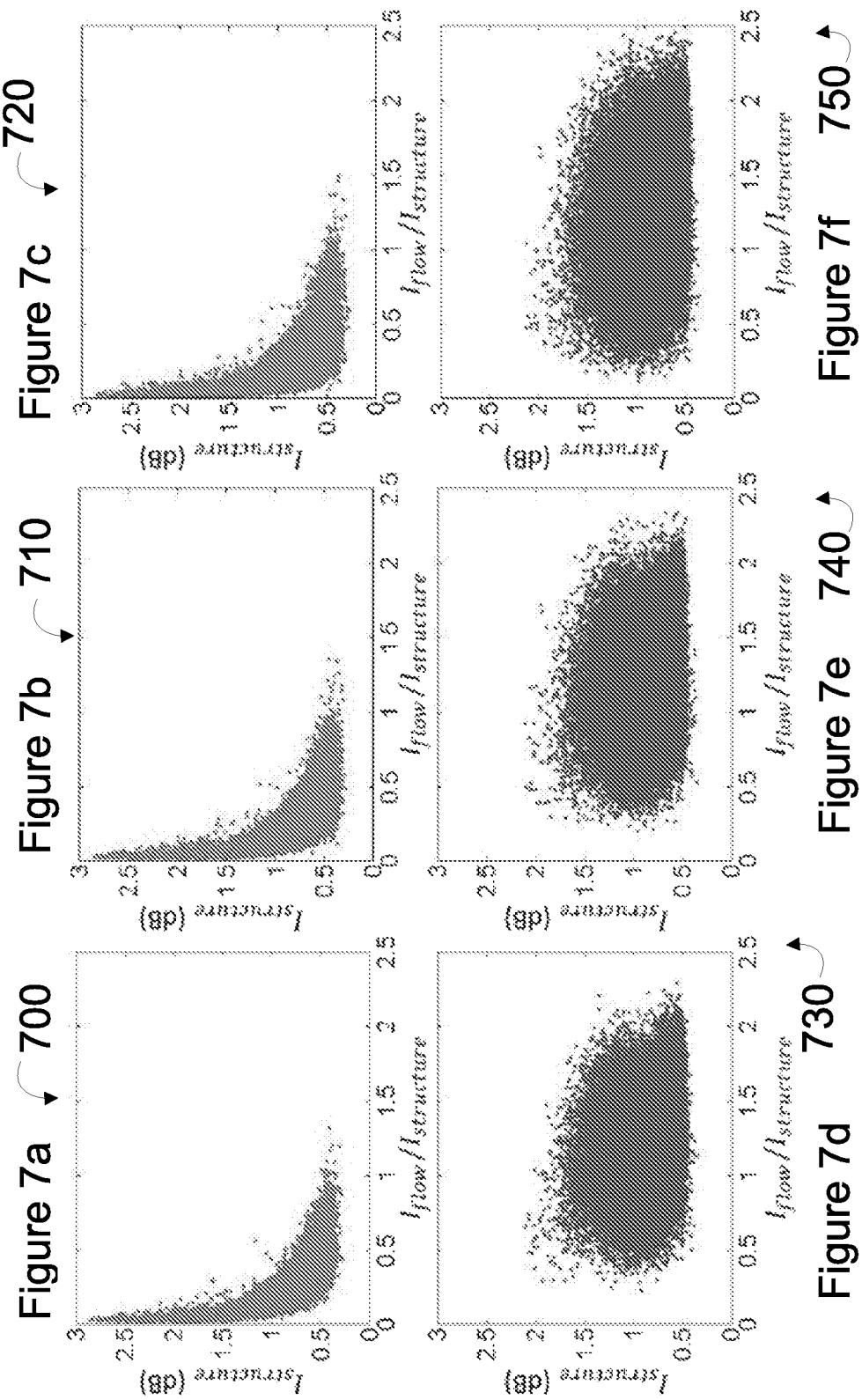

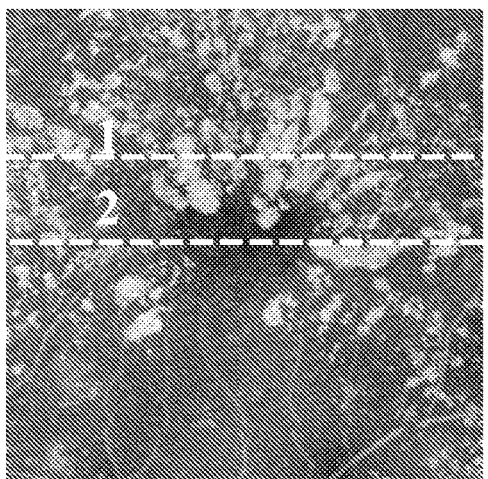
Figure 9a 900  Figure 9b 910
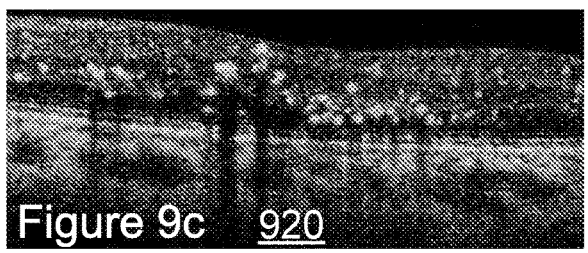
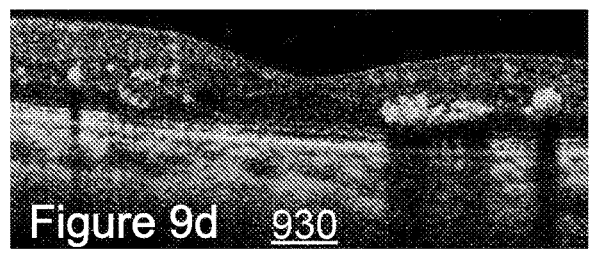
Figure 9c 920  Figure 9d 930
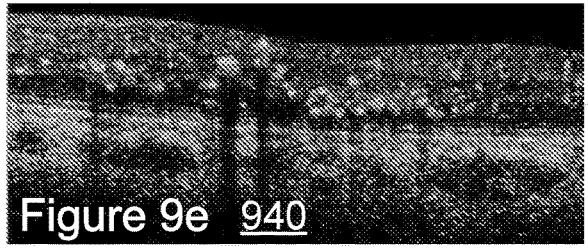
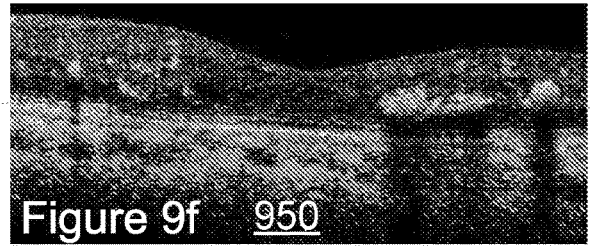
Figure 9e 940  Figure 9f 950
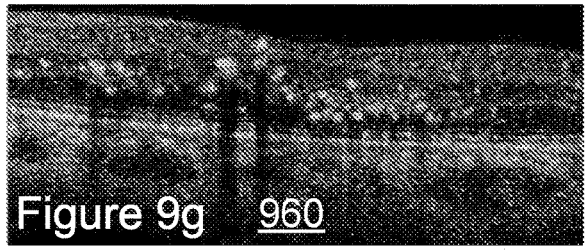
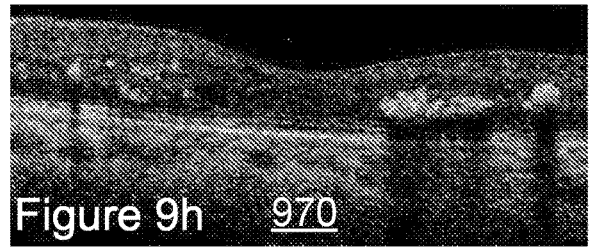
Figure 9g 960  Figure 9h 970
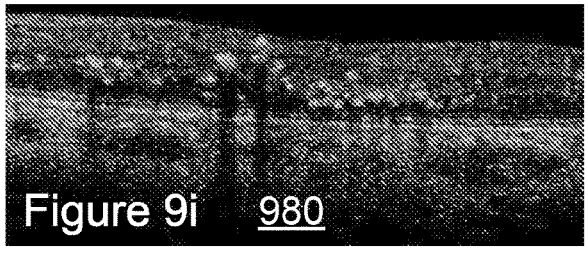
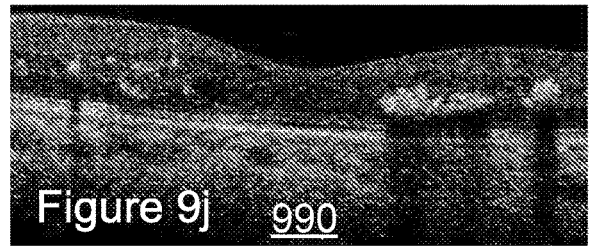
Figure 9i 980  Figure 9j 990

Figure 10a 1000
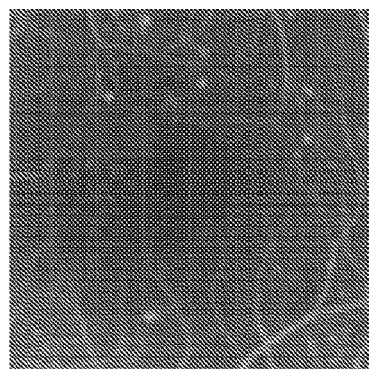
Figure 10b 1050
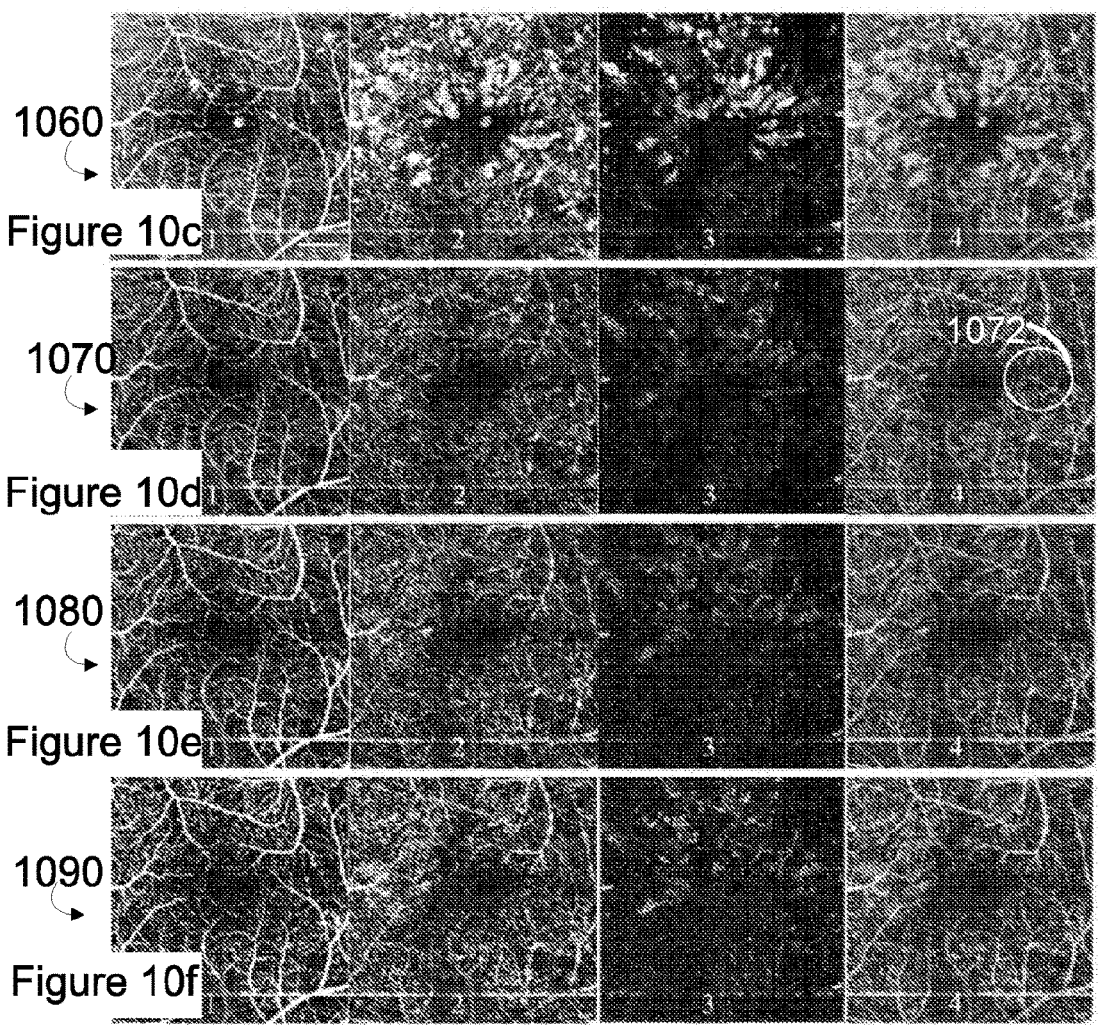
Figure 10c 1060
Figure 10d 1070
Figure 10e 1080
Figure 10f 1090

METHODS AND SYSTEMS FOR ENHANCING MICROANGIOGRAPHY IMAGE QUALITY

CROSS-REFERENCE TO RELATED APPLICATIONS

This application claims priority to U.S. Provisional Patent Application Ser. No. 62/129,410 filed on Mar. 6, 2015, which is hereby incorporated by reference in its entirety.

STATEMENT REGARDING FEDERALLY SPONSORED RESEARCH

This invention was made with U.S. government support under Grant No. R01 EY024158, awarded by the National Institutes of Health. The government has certain rights in the invention.

BACKGROUND

Retinal microcirculation is important in maintaining normal visual functions, providing oxygen and nutrients to active retinal tissue, and removing metabolites and waste from the tissue. Retinal pathologies can cause alteration in the retinal vascular network and affect photoreceptor function, which may lead to a significant loss of vision. Visualizing such alterations in retinal vasculature is thus desirable.

Fluorescein angiography (FA) is a minimally invasive method used for the clinical investigation and diagnosis of the vascular change in a retina. However, due to its relatively low spatial resolution and lack of depth information, it is difficult to obtain detailed information of the pathology, such as the location of affected vessels and the specific morphological changes in the capillary network.

OCT has been used for both structural and functional imaging of the posterior eye, and retinal blood flow based on the principle of the Doppler phenomenon. However, Doppler based flow detection is dependent on the Doppler angle, which is insensitive to the particle movement perpendicular to the probing beam, and most of the retinal blood vessels run almost perpendicular to the incident OCT probe beam.

Optical microangiography (OMAG) is an optical coherence tomography (OCT) based imaging technique used for angiographic imaging of biological tissues in vivo. The OMAG method extracts blood flow information based on a direct differentiation of complex or intensity OCT signals between repeated B-scans acquired at the same cross-section. The OMAG method is sensitive to blood cell movement and thereby provides a high imaging resolution.

However, in OMAG, the acquired signals from static background within repeated B-scans are not exactly the same due to, for example, sample movement, system noise, and stability in scanning mechanisms. Thus, the angiographic results not only contain flow information but also bear a static background signal. Such "false flow" is difficult to differentiate from real blood flow based on flow images alone. Additionally, OMAG is prone to artifacts due to tissue hyper-reflection, which is commonly seen in retinal diseases.

SUMMARY

In accordance with the present invention, a system and a method are defined for enhancing quality of a flow image of a sample of a subject. In one embodiment, the computer-implemented method may comprise acquiring a first flow image from a plurality of first OMAG scans of the sample. The sample comprises a biological tissue having fluid flow therethrough. The method includes acquiring a structure image from a second OMAG scan of the sample, plotting, onto a graph, data based on pixel intensity values from the flow image and pixel intensity values from the structure image and differentiating the data, based on location on the graph, into a first data group representing static structure signals and a second data group representing flow signals. The method then includes suppressing pixels in the flow image corresponding to the first data group. The graph may be a two-dimensional (2D) graph or a three-dimensional (3D) graph. The fluid flow may be a blood flow, and the method may further comprise quantifying blood perfusion within the biological tissue in the image.

In one example embodiment, the method may further comprise setting pixels with a probability greater than a threshold to zero intensity on the flow image.

Plotting data based on pixel intensity values from the flow image and pixel intensity values from the structure image may comprise plotting a logarithm of structural pixel intensity over a ratio of flow pixel intensity to structural pixel intensity. In one example embodiment, only data having pixel intensity values above a noise level are plotted onto the graph.

Differentiating the data by location on the graph may comprise determining a boundary on the graph between the first data group and the second data group.

Acquiring the first flow image from the plurality of first OMAG scans of the sample may comprise generating the first flow image from a plurality of adjacent B-scans of the sample.

In another embodiment, a method for reducing artifacts in an image of a sample of a subject is provided. The method comprises extracting at least one flow signal from a plurality of optical microangiography (OMAG) scans of the sample, wherein the sample comprises a biological tissue having fluid flow therethrough, multiplying the at least one flow signal by a weighting factor comprising a motion index to produce at least one weighted flow signal to suppress artifacts, and displaying an image of the sample from the at least one weighted flow signal. The OMAG scans may comprise a plurality of adjacent B-scans of the sample.

In one example embodiment, the motion index is an inter-frame pixel decorrelation coefficient.

In another example embodiment, the method comprises compressing the at least one weighted flow signal with a threshold. The weighted flow signal may be generated from the structural image.

In some example embodiments, the sample comprises one of the following: a brain, an eye, a retina, a tumor, a heart, skin, a kidney, a gastroenterology tract, a productive system, and a cochlear. The method may be used in imaging cerebrovascular perfusion, retinal microcirculation, tumor progression, posterior eye vascular imaging, or angiography, among other applications.

In yet another embodiment, a system for in vivo imaging is provided. The system comprises an OMAG apparatus configured to generate images from living tissue, and a non-transitory computer-readable medium having stored therein instructions executable to cause a computing device to carry out a method comprising acquiring a first flow image from a plurality of first optical microangiography (OMAG) scans of the sample. The sample comprises a biological tissue having fluid flow therethrough. The method further comprises acquiring a structure image from a second OMAG scan of the sample, plotting, onto a graph, data based on pixel intensity values from the flow image and pixel intensity values from the structure image, and differentiating the data, based on location on the graph, into a first data group representing static structure signals and a second data group representing flow signals. The method then comprises suppressing pixels in the flow image corresponding to the first data group.

In yet another embodiment, a system for in vivo imaging is provided. The system comprises an OMAG apparatus configured to generate images from living tissue and a non-transitory computer-readable medium having stored therein instructions executable to cause a computing device to carry out a method comprising extracting at least one flow signal from a plurality of OMAG scans of the sample, wherein the sample comprises a biological tissue having fluid flow therethrough, multiplying the at least one flow signal by a weighting factor comprising a motion index to produce at least one weighted flow signal to suppress artifacts, and displaying an image of the sample from the at least one weighted flow signal.

These as well as other aspects and advantages of the synergy achieved by combining the various aspects of this technology, that while not previously disclosed, will become apparent to those of ordinary skill in the art by reading the following detailed description, with reference where appropriate to the accompanying drawings.

BRIEF DESCRIPTION OF THE FIGURES

FIG. 3a depicts a structural image of a solid phantom, in accordance with at least one embodiment;

FIG. 3b depicts a structural image of a lipid phantom, in accordance with at least one embodiment;

FIG. 3c depicts a flow image of the solid phantom of FIG. 3a, in accordance with at least one embodiment;

FIG. 3d depicts a flow image of the lipid phantom of FIG. 3b, in accordance with at least one embodiment;

FIG. 3e depicts a graph plotting a logarithm of pixel intensity from structure images of FIGS. 3a-b over a ratio of flow image pixel intensity and structure image pixel intensity from the images of FIGS. 3a-d, in accordance with at least one embodiment;

FIG. 3f depicts a graph incorporating a Gaussian process classification to the data of FIG. 3e, in accordance with at least one embodiment;

FIG. 4a depicts a structural image of a phantom containing both solid and liquid 2% intralipid, in accordance with at least one embodiment;

FIG. 4b depicts an image of the phantom of FIG. 4a after application of the feature space OMAG methodology (fsOMAG), in accordance with at least one embodiment;

FIG. 4c depicts an image of the phantom of FIG. 4a after application of traditional OMAG methodology, in accordance with at least one embodiment;

FIG. 5a depicts a B-scan image that applied an fsOMAG methodology, in accordance with at least one embodiment;

FIG. 5b depicts a B-scan image that applied a traditional OMAG methodology, in accordance with at least one embodiment;

FIG. 5c depicts a maximum intensity projection enface view of a retinal blood vessel network acquired using an fsOMAG method, in accordance with at least one embodiment;

FIG. 5d depicts a maximum intensity projection enface view of a retinal blood vessel network acquired using a traditional OMAG method, in accordance with at least one embodiment;

FIG. 5e depicts an image of the blood vessel network in the nerve fiber layer (NFL) of a subject obtained using an fsOMAG method, in accordance with at least one embodiment;

FIG. 5f depicts an image of the blood vessel network in the NFL of a subject obtained using a traditional OMAG method, in accordance with at least one embodiment;

FIGS. 7a-7c depict feature space projections of liquid phantoms under three, four, and five B-scan repetitions, in accordance with at least one embodiment;

FIGS. 7d-7f depict feature space projections of solid phantoms corresponding to the liquid phantoms of FIGS. 7a-7c, in accordance with at least one embodiment;

FIG. 9a depicts an OCT structural projection image of retinal tissue between the ganglion cell layer and the external limiting membrane, in accordance with at least one embodiment;

FIG. 9b depicts an OCT structural projection image of the posterior eye, in accordance with at least one embodiment;

FIG. 9c depicts an image for detecting blood flow in a B-scan at Line 1 from FIG. 9a, in accordance with at least one embodiment;

FIG. 9d depicts an image for detecting blood flow in a B-scan at Line 2 from FIG. 9a, in accordance with at least one embodiment;

FIG. 9e depicts an image for detecting blood flow in a B-scan at Line 1 from FIG. 9a, in accordance with at least one embodiment;

FIG. 9f depicts an image for detecting blood flow in a B-scan at Line 2 from FIG. 9a, in accordance with at least one embodiment;

FIG. 9g depicts an image for detecting blood flow in a B-scan at Line 1 from FIG. 9a, in accordance with at least one embodiment;

FIG. 9h depicts an image for detecting blood flow in a B-scan at Line 2 from FIG. 9a, in accordance with at least one embodiment;

FIG. 9i depicts an image for detecting blood flow in a B-scan at Line 1 from FIG. 9a, in accordance with at least one embodiment;

FIG. 9j depicts an image for detecting blood flow in a B-scan at Line 2 from FIG. 9a, in accordance with at least one embodiment;

FIG. 10a depicts an image illustrating segmentation of three retinal layers of an eye of a subject, in accordance with at least one embodiment;

FIG. 10b depicts an enlarged view of a portion of the image of FIG. 10a, in accordance with at least one embodiment;

FIG. 10c depicts an en face vascular image series of the different layers of FIG. 10a using an OMAG method, in accordance with at least one embodiment;

FIG. 10d depicts an en face vascular image series of the different layers of FIG. 10a using a weighted OMAG methodology (wOMAG), in accordance with at least one embodiment;

FIG. 10e depicts an en face vascular image series of the different layers of FIG. 10a using a CA1 method, in accordance with at least one embodiment;

FIG. 10f depicts an en face vascular image series of the different layers of FIG. 10a using a CA2 method, in accordance with at least one embodiment;

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

Angiography methods, such as OMAG, provide for the visualization of functional blood vessels noninvasively and with exceptional sensitivity. Yet such methods are prone to capturing static background based on repeated scans and hyper-reflection signals from highly reflecting structures. Minimizing static background is difficult due to the difficulty in delineating static background signals from flow signals. Suppressing hyper-reflection signals often compromises visibility of the vascular structure. The methods and systems provided herein maximize the signal of flow while minimizing the background static signal, as well as suppress hyper-reflection signals while maintaining the detected capillary networks.

Figure 1:
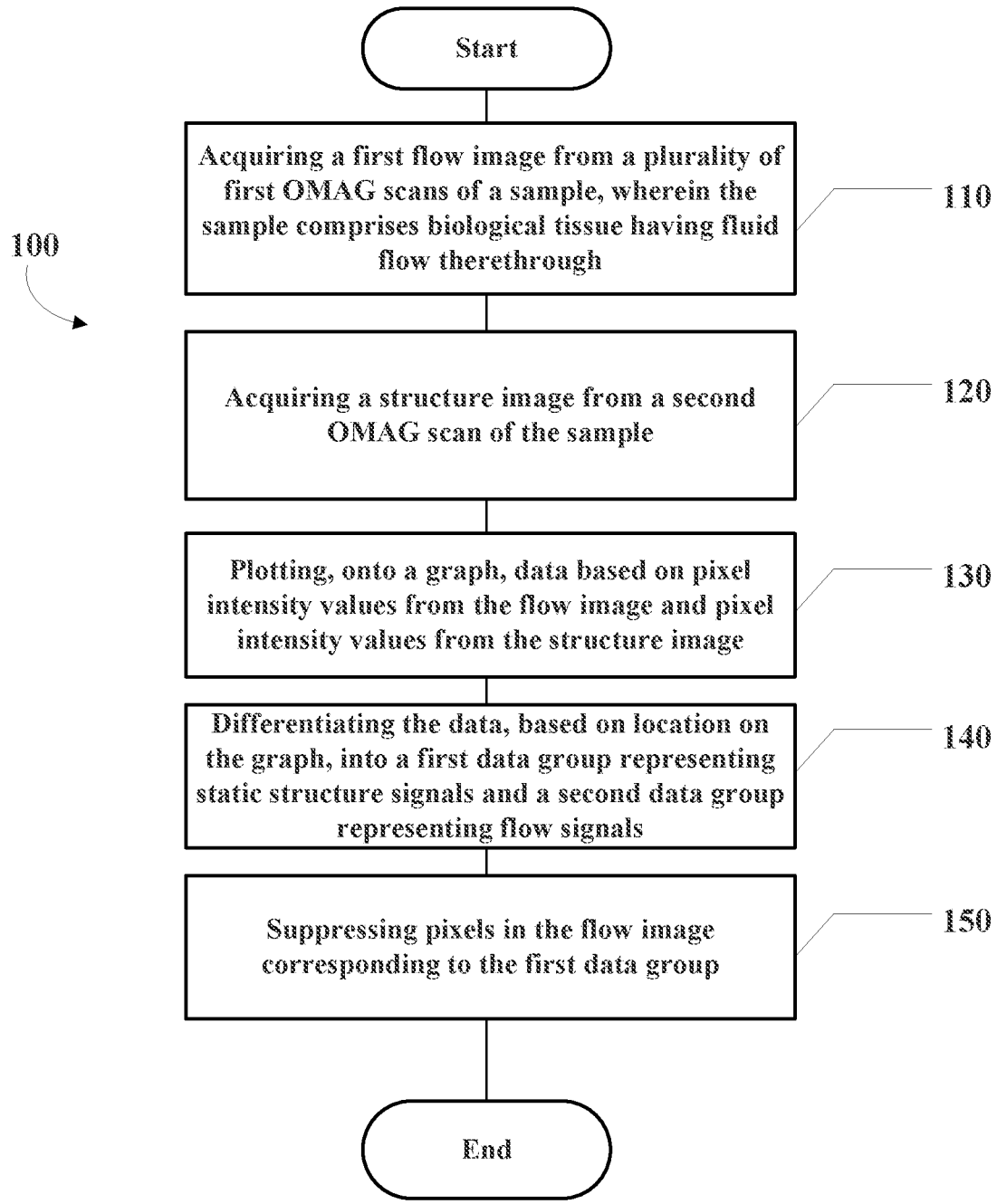
FIG. 1 depicts a simplified flow diagram of an example method that may be carried out to enhance quality of a flow image of a sample of a subject, in accordance with at least one embodiment.

FIG. 1 depicts a simplified flow diagram of an example method 100 that may be carried out to enhance quality of a flow image of a sample of a subject, in accordance with at least one embodiment.

As referenced herein, a subject may be a human subject, and may be an adult human subject, an adolescent human subject, an infant human subject, or a newborn human subject. The sample may be an in vivo sample.

For the method 100 and other processes and methods disclosed herein, the flowchart shows functionality and operation of one possible implementation of the present embodiments. In this regard, each block may represent a module, a segment, or a portion of program code, which includes one or more instructions executable by a processor for implementing specific logical functions or steps in the process. The program code may be stored on any type of computer readable medium, for example, data storage including a one or more computer-readable storage media that may be read or accessed by the processor, and may be a fixed or removable hard drive, a flash memory, a rewritable optical disk, a rewritable magnetic tape, or some combination of the above. The computer readable medium may include a physical and/or non-transitory computer readable medium, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable medium may also be any other volatile or non-volatile storage system. The computer readable medium may be considered a computer readable storage medium, a tangible storage device, or other article of manufacture, for example. Alternatively, program code, instructions, and/or data structures may be transmitted via a communications network via a propagated signal on a propagation medium (e.g., electromagnetic wave(s), sound wave(s), etc.).

Initially, the method 100 includes acquiring a first flow image from a plurality of first OMAG scans of a sample, wherein the sample comprises biological tissue having fluid flow therethrough, at block 110. A plurality of adjacent B-scans, or repeated B-scans at one location, of the sample may be used as the plurality of first OMAG scans.

The method 100 then includes acquiring a structure image from a second OMAG scan of the sample, at block 120.

The flow image and the structure image are pixelated images, each comprising a plurality of pixels with varying intensity values that represent and display structures within the sample.

The method 100 includes plotting, onto a graph, data based on pixel intensity values from the flow image and pixel intensity values from the structure image, at block 130. The graph may be a 2D graph or a 3D graph, and is also referred to herein as a "feature space," wherein data obtained from the pixel intensity values are plotted in or projected onto the feature space. A 2D graph may be based on the structure image data and the flow image data, providing a 2D plane. Other results may be added, such as a phase difference image, for example, to generate a 3D plane and thus a 3D graph.

Each data point is projected onto a location on the feature space based on pixel intensity. In one example embodiment, a logarithm of structural pixel intensity is plotted over a ratio of flow pixel intensity to structural pixel intensity. In one example embodiment, only data having pixel intensity values above a noise level are plotted on the graph.

In some example embodiments, a classification map may also be generated on the feature space that provides criterion for classification of pixels representing flow and pixels representing static background. In such an example embodiment, the classification map comprises prior obtained data used to calculate a probability distribution of data designating flow signals and data designating structure signals. Such a classification map may be generated prior to carrying out method 100. A predictive probability in the feature space may be generated for use with method 100 based on the posterior probability obtained from generating a classification map prior to carrying out method 100.

In some example embodiments, the prior obtained data is taken from a subject in vivo. However, it can be difficult to identify static scattering tissue in an in vivo scenario.

In some example embodiments, the prior obtained data is taken from a phantom sample. As used herein, a "phantom" is a substance or combination of substances configured to closely mimic desired optical properties of a biological tissue. For an application involving assessment of an optical tissue, a phantom configured to have similar absorption and scattering properties as biological tissue, such as comprising optical scattering particles, (e.g., a lipids emulsion or Titanium oxide, suspended in a gel or water) is used. Titanium oxide may also be mixed into resin to act as a phantom. In the embodiment wherein a lipid emulsion is used, the emulsion is configured to simulate the scattering properties of biological tissues; specifically, the response of biological tissues to light at wavelengths in the visible and infrared or near-infrared ranges where the tissue highly scatters the light but has a low absorption coefficient. The lipid emulsion is configured to respond in a similar manner to how the biological tissue would act when subjected to the same imaging modality (e.g., an OMAG imaging modality). In one example embodiment, Intralipid® may be used as a lipid emulsion to generate the phantom, wherein Intralipid® is an emulsion of soy bean oil, egg phospholipids, and glycerin. For example, a phantom made of 2% Intralipid® and 98% water may be scanned. In one example embodiment, a phantom may be a solidified gel phantom, wherein a solidified gel is a jelly-like material that exhibits no flow when in the steady-state, is mixed with a low concentration lipid (e.g., 0.01% to 10%) to mimic static tissue. In another example embodiment, a phantom may comprise a light-scattering lipid solution comprising lipids suspended in water to mimic the flow.

The method then includes differentiating the data, based on location on the graph, into a first data group representing static structure signals and a second data group representing flow signals, at block 140. The predictive probability of certain data in the feature space comprising flow data and other data comprising static background data may be used to more clearly differentiate the data. A boundary may be determined on the graph between the first data group and the second data group. An example of such a boundary is provided as boundary 352 in FIG. 3f, discussed below.

The method then includes suppressing pixels in the flow image corresponding to the first data group, at block 150.

The method 100 provides for effective differentiation of flow signals from static background, which may be used to then suppress unwanted static background signals and thus enhance the quality of an image. By plotting the data on the feature space, it is possible to differentiate the flow signals from the static signals without the use of contrast mechanisms, such as dyes, being introduced into the sample. Thus, the method 100 provides a non-invasive differentiation mechanism. The method 100 may be performed for a number of biomedical imaging applications, such as in the imaging of cerebrovascular perfusion, retinal microcirculation, tumor progression, posterior eye vascular imaging, or angiography, for example.

Figure 2:
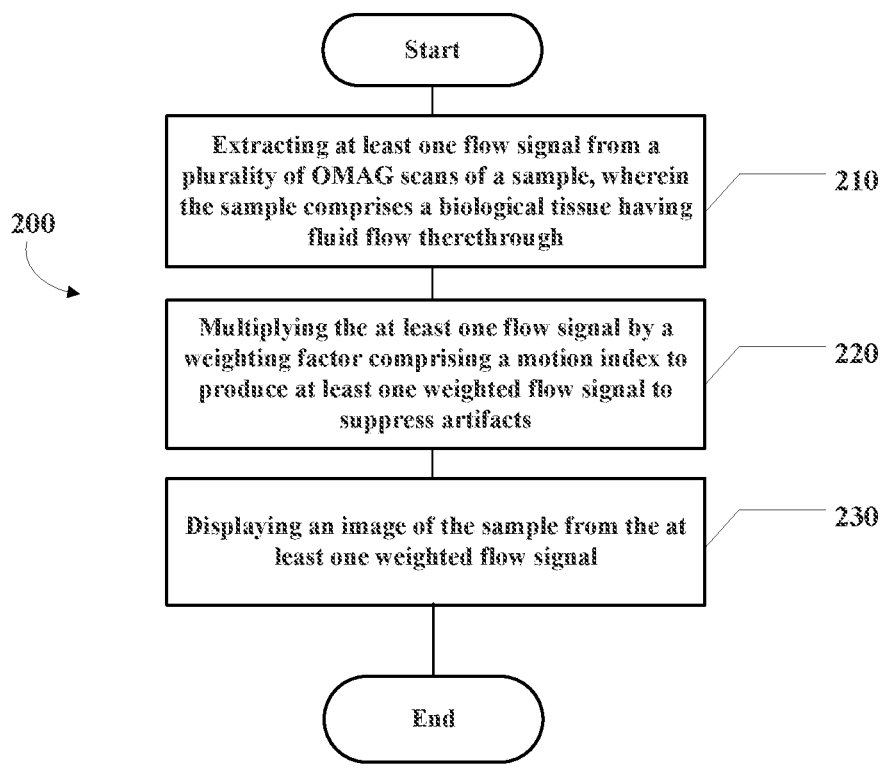
FIG. 2 depicts a simplified flow diagram of an example method that may be carried out to reduce artifacts in an image of a sample of a subject, in accordance with at least one embodiment.

FIG. 2 depicts a simplified flow diagram of an example method 200 that may be carried out to reduce artifacts in an image of a sample of a subject, in accordance with at least one embodiment. The method 200 provides for the suppression of artifacts caused by hyper-reflection, while optimally maintaining visibility and connectivity of the capillary network in OCT angiographic imaging.

The intensity of false flow pixels is expected to be higher than the intensity of pixels of real flow. The present method 200 uses this difference in intensity to classify static and flow pixels.

Initially, the method 200 includes extracting at least one flow signal from a plurality of OMAG scans of the sample, wherein the sample comprises a biological tissue having fluid flow therethrough, at block 210. The sample may be an in vivo sample. In some example embodiments, the sample comprises at least a portion of a human eye. In other example embodiments, the sample comprises at least a portion of a brain, a tumor, a heart, a kidney, a gastroenterology tract, a productive system, a cochlear, skin, or a blood vessel, among others.

An OCT angiography system, such as an OMAG system, may acquire a plurality of adjacent B-scans, or repeated B-scans of the sample.

The method then includes multiplying the at least one flow signal by a weighting factor comprising a motion index to produce at least one weighted flow signal to suppress artifacts, at block 220, where the motion index is derived from inter-frame (or inter-B-scan) pixel decorrelation coefficient.

Figure 8C:
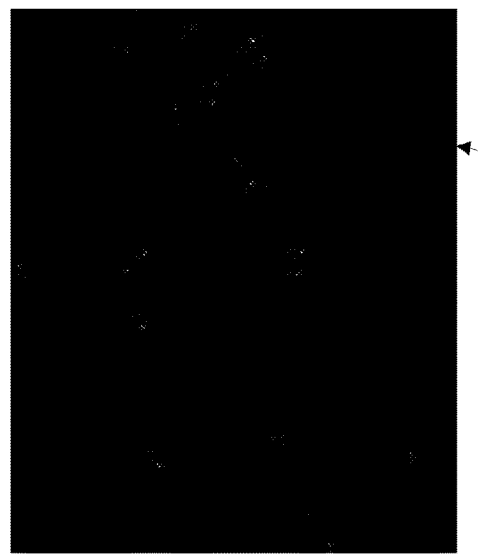
FIG. 8c depicts a flow image of the phantom of FIG. 8a after data processing using a weighted OMAG methodology (wOMAG), in accordance with at least one embodiment.

The method includes displaying an image of the sample from the at least one weighted flow signal, at block 230. The image provides a clearer view of the structures within the tissue as the artifacts are suppressed through application of the weighted flow signal. An example displayed image is depicted in FIG. 8c, further described below.

The method 200 may additionally comprise compressing the at least one weighted flow signal, wherein the weighted flow signal is generated from the structural image.

In another embodiment of method 200, the suppression of hyper-reflection artifacts takes advantage of structural image of the sample because the hyper-reflection artifact in the flow image, f(x,y), typically corresponds to the high-reflection signals seen in the structural image, s(x,y). To suppress the hyper-reflection artifacts in flow image, the structural image is first normalized into a value range [0 1], which is then inverted to become an image with a range of [1 0]. Finally, the flow image is modified by the operation below:

$$f_M(x,y) = f(x,y) * \{1 - \text{Norm}(-[s(x,y)])\} \quad [1]$$

where Norm[s(x,y)] represents normalization operation. The resulting image $f_M(x,y)$ would then be an image with hyper-reflection suppressed. In another embodiment, Equation 1 may be written as:

$$f_M(x,y) = f(x,y) * \{1 - \text{Norm}[s(x,y)]^\alpha\}^\beta \quad [2]$$

where the scaling $\alpha$ and $\beta$ can be any values between 0 and 100.

The method 200 provides a low cost solution for effectively suppressing artifacts in OCT angiographic imaging applications. The method 200 may be useful in applications such as to image normal retina where the reflection of one or more layers within the retina is strong, including the nerve fiber layer (NFL) and the retinal pigment epithelium (RPE). Furthermore, because hyper-reflection is commonly seen in a number of posterior eye pathologies, including but not limited to diabetic retinopathy (DR), age-related macular degeneration (AMD), and macular telangiectasia, for example, the method 200 may be useful for diagnosing, prognosing, and monitoring a number of ocular pathologies. Further, the method 200 may be useful for diagnosing, prognosing, and monitoring a number of brain, blood vessel, kidney, skin, heart, gastrointestinal, cochlear, and productive system pathologies, as well as other pathologies of the human body, including tumors.

For methods 100 and 200, the structural and flow images may be the direct images from an OCT/OMAG system. In another embodiment, the structural and flow images may be compressed images, for example logarithmically compressed, from an OCT/OMAG system. In yet another embodiment, the structural and flow images may be direct, compressed or combined images, from an OCT/OMAG system.

Thus, methods 100 and 200 provide for enhancing quality of a flow image with high accuracy. The methods 100 and 200 are not limited to ophthalmology applications, and the sample to be imaged may comprise the brain, a tumor, skin, a kidney, a gastroenterology tract, a productive system, and a cochlear, for example. Other parts of the human body may also be imaged using the methods 100 and 200.

II. Example Image Enhancement Methods

In a recent study, a classification map was generated on a feature space to differentiate flow and structure pixels in an image for the purpose of image enhancement. In the study, two phantoms made of 2% Intralipid® solution were fabricated to generate the classification map.

FIG. 3a depicts a structural image 300 of a solid phantom, in accordance with at least one embodiment. The solid phantom is a solidified gel phantom mixed with low concentration lipid (about 2%) to mimic static tissue.

FIG. 3b depicts a structural image 310 of a lipid phantom, in accordance with at least one embodiment. The lipid phantom is a scattering lipid solution (about 2%) to mimic flow of blood through biological tissue.

Corresponding flow images were generated from the average of differences among five repeated B-scans, using an OCT system operating in 1300 nm with measured axial resolution of 13 µm in air and a lateral resolution of 6 µm. FIG. 3c depicts a flow image 320 of the solid phantom of FIG. 3a, in accordance with at least one embodiment. Hyper-reflection of the solid phantom is indicated by circle 322 in FIG. 3c. FIG. 3d depicts a flow image 330 of the lipid phantom of FIG. 3b, in accordance with at least one embodiment.

FIG. 3e depicts a graph 340 plotting a logarithm of pixel intensity from structure images over a ratio between pixel intensity for flow images and pixel intensity for structure images from the images of FIGS. 3a-d, in accordance with at least one embodiment. The graph 340 is an example embodiment of the graph discussed with reference to the method 100 in FIG. 1. In the present study, the graph 340 was a 2D feature space projection. The logarithm of pixel intensity from the structural images comprised base $\log_{10}$ ($I_{structure}$), which was plotted on the y-axis of the feature space. The ratio between the pixel intensity for flow images and the pixel intensity for structure images is represented by ($I_{flow}/I_{structure}$), plotted on the x-axis of the feature space.

The graph 340 indicates that most of the pixels representing flow 342 are well separated from the pixels representing static structure 344. There is some overlapping for pixels with low structural intensities 346 due to system noise. Additionally, the hyper-reflection of the solid phantom that might lead to false flow signals on the flow image, indicated by circle 322 in FIG. 3c, is shown to be located far apart from flow pixels as indicated by the circle 348 in FIG. 3e.

A Gaussian process classification (GPC) was then applied to generate a classification map in the feature space to separate the static and the flow signals. GPC is a probabilistic statistical model based on logistic regression, which predicts the probability distribution of the data belonging to one particular group. The predictive probability is calculated using the following equation:

$$p(t_{N+1}=1/\vec{t}_N)=\int p(t_{N+1}=1/a_{N+1})p(a_{N+1}/\vec{t}_N)da_{N+1} \quad [3]$$

where $\vec{t}_N$ is the training dataset, $p(t_{N+1}=1/a_{N+1})$ is calculated from the sigmoid function $\sigma(a_{N+1})$, and $p(a_{N+1}/\vec{t}_N)$ is the posterior probability obtained from $p(a_N/\vec{t}_N)$ which is calculated based on Laplacian approximation through learning and where $\vec{a}_N$ is an implicit function over training dataset that can be transformed into posterior probability via logistic sigmoid.

FIG. 3f depicts a graph 350 incorporating a classification map based on GPC to the data of FIG. 3e, in accordance with at least one embodiment. The values on the graph 350 represent the probability of each pixel projected in the feature space. A boundary 352 is shown separating the two groups of data, flow data versus structure data. The boundary was generated by setting $p(t_{N+1}=1/\vec{t}_N)=0.5$. The curve shape in boundary 352 was unknown until the present study, and illustrates the difficulty in separating the flow signal from static background using a simple thresholding method. Indeed, it is often observed from in vivo data that the angiographic outcomes are hindered by static background signals that are difficult to remove via simple thresholding; manual operation such as segmentation or single vessel tracing are employed to remove such background signals. The methods discussed herein provide a more accurate separation of flow signals and static signals, as demonstrated by the curve 352 in FIG. 3f, than simple thresholding would accomplish, thereby eliminating the need for laborious manual separation steps.

After the experimental data was acquired and projected onto the graph 350, thereby generating a classification map, a flow image and a static image of the sample were obtained using the same OCT method as for the experimental data. The pixel intensities from both the flow and structure images were then processed using the same equations as for the experimental pixel intensity data, and were also projected onto the graph 350. The static background was then differentiated from the flow signals with use of the boundary 352 generated from the experimental data.

Thereafter, the pixels with a probability larger than 0.5 on the graph 350 were set to zero when processing the flow image for display, effectively suppressing the static background. The higher the threshold is set, the more flow signals will be included; however, the chance for including static signals is also increased. In an alternative embodiment, pixels with probability smaller than 0.5 in the graph may be set to 65535 on the 16-bit flow image, greatly increasing the flow signals. However, doing so would correspondingly eliminate the useful information of the flow, for example, particle concentration, which is embedded within the OMAG signals.

FIGS. 4a-c depict images of a phantom for analysis using the image enhancement method 100 of FIG. 1, also referred to herein as feature space OMAG (fsOMAG).

FIG. 4a depicts a structural image 400 of a phantom containing both solid and liquid 2% intralipid, in accordance with at least one embodiment. As shown in image 400, the liquid lipid portion 402 of the phantom is located above the solid portion 404 and is shown to have a different texture from the solid portion 404. Also shown in image 400 are two circles 406 containing hyper-reflections at an air-phantom interface 408.

FIG. 4b depicts an image 410 of the phantom of FIG. 4a after application of the fsOMAG methodology, in accordance with at least one embodiment. The fsOMAG process results in an image where the static background is suppressed. Further, the circles 406 containing hyper-reflections at the air-phantom interface 408 are also shown to be excluded.

FIG. 4c depicts an image 420 of the phantom of FIG. 4a after application of traditional OMAG, in accordance with at least one embodiment. The OMAG methodology leads to better differentiation and suppression of the solid portion 404 than that provided in the image 400; however, the signals from static background are still obvious. The difference in the static background is observable when comparing the solid portions 404 of FIG. 4b with FIG. 4c.

In another study, an in vivo human posterior eye was imaged using an OCT system, and the retinal blood vessel network within the macular region was examined using fsOMAG and traditional OMAG methodologies.

FIG. 5a depicts a B-scan image 500 that applied an fsOMAG method, in accordance with at least one embodiment. The fsOMAG method applied to obtain the image 500 applied the image enhancement method 100 of FIG. 1. The OCT system operated at a 147 kHz A-scan rate, with 12 µm measured axial resolution in the air and approximately 13 µm lateral resolution at the retinal surface. An approximate 1.8 mW light power was applied at the cornea, below the safe ocular exposure limits recommended by the American National Standards Institute. The measurements were conducted in normal daylight conditions without pupil dilation. The OCT system ran at 393 B-scans per second. The time period for each data set acquisition was approximately 4 seconds.

FIG. 5b depicts a B-scan image 510 that applied a traditional OMAG method, in accordance with at least one embodiment. As can be seen, image 500 not only minimizes the static background noise, but also increases the flow signals, as compared to image 510. Arrows 502, shown in image 500, show that the tailing effect is still visible, however.

FIG. 5c depicts a maximum intensity projection enface view 520 of a retinal blood vessel network acquired using an fsOMAG method, in accordance with at least one embodiment. FIG. 5d depicts a maximum intensity projection enface view 530 of a retinal blood vessel network acquired using a traditional OMAG method, in accordance with at least one embodiment. The blood vessel network shown in FIGS. 5c and 5d comprises the NFL, the ganglion cell layer (GCL), the inner plexiform layer (IPL), and the outer plexiform layer (OPL). The areas indicated by circles 522 illustrate how in FIG. 5d, blood vessels are overwhelmed by the static background signals (mainly resulting from the nerve fiber layer due to its high reflectance), resulting in a denser network shown, whereas in the same areas in FIG. 5c, the vessel network is more clearly visualized and not obscured by the static background signals, which are suppressed. The NFL typically has to be manually removed to obtain a clear enface view using traditional OMAG methods. A box 502 is depicted in the image 520 for further analysis and discussion with reference to FIG. 6b below.

FIG. 5e depicts an image 540 of the blood vessel network in the NFL of a subject obtained using an fsOMAG method, in accordance with at least one embodiment. FIG. 5f depicts an image 550 of the blood vessel network in the NFL of a subject obtained using a traditional OMAG method, in accordance with at least one embodiment. As indicated by the arrows 542, image 540 shows clearer vasculature results than image 550.

Figures 6A, 6B:
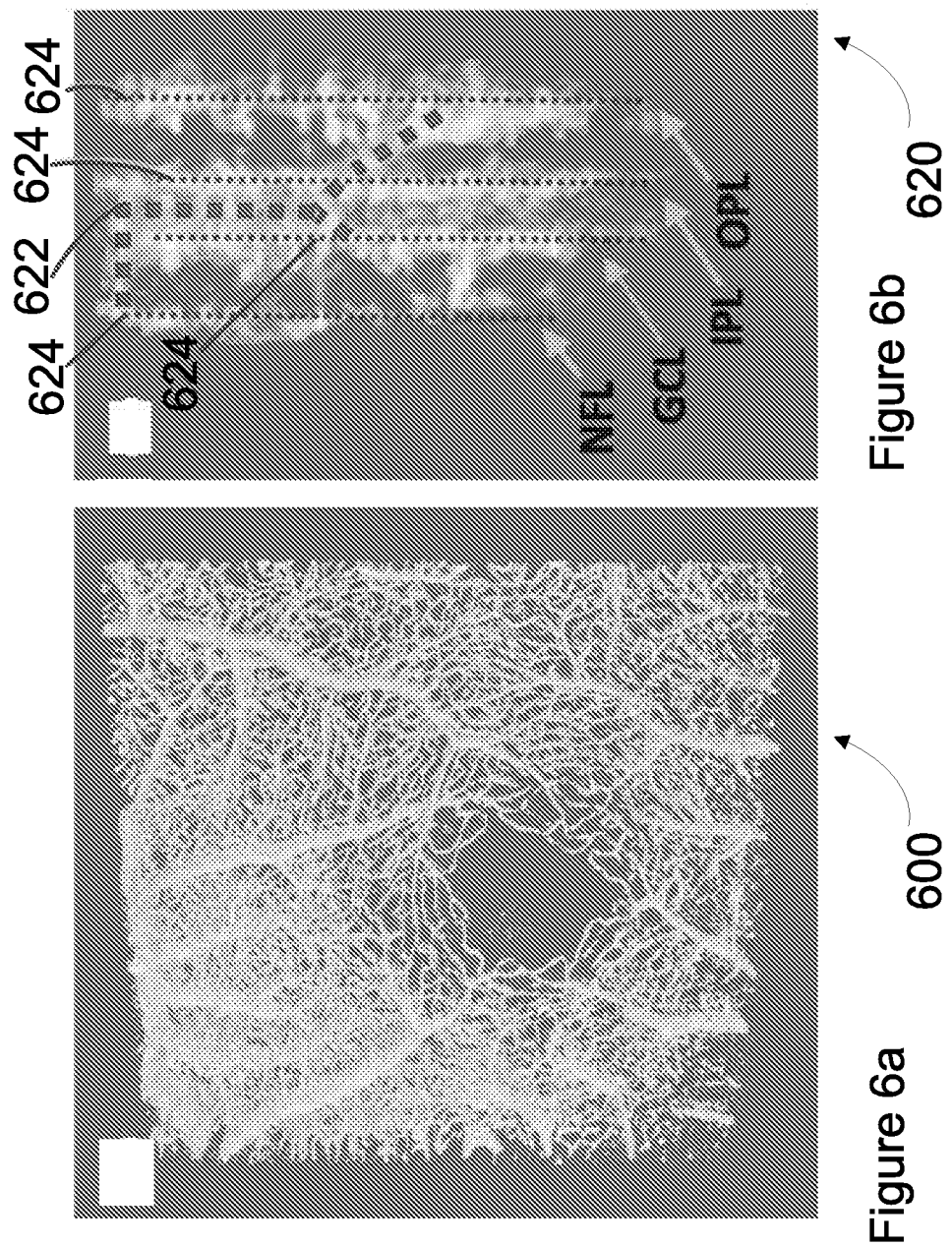
FIG. 6a depicts a representative image of a retinal vessel network in 3D space, in accordance with at least one embodiment.
FIG. 6b depicts a profile image of a 3D space of the box depicted in FIG. 5c, in accordance with at least one embodiment.

The superior performance of fsOMAG provides an opportunity to visualize the retinal blood vessel network in true 3D space. FIG. 6a depicts a representative image 600 of a retinal vessel network in 3D space, in accordance with at least one embodiment. FIG. 6b depicts an image 620 at a side view or profile of the 3D space of the box 502 depicted in FIG. 5c, in accordance with at least one embodiment. As shown in image 620, large vessels indicated by dotted lines 622 feed the capillaries indicated by dotted lines 624 in the NFL, GCL, IPL, and OPL. This ability of in vivo visualization of the retinal vessel structures in three dimensions may be useful in the study of intravascular related conditions and pathologies.

FIGS. 7a-7c depict the feature space projections 700, 710, and 720 of liquid phantoms under three, four, and five B-scan repetitions, respectively, in accordance with at least one embodiment. FIGS. 7d-7f depict feature space projections 730, 740, and 750 of solid phantoms corresponding to the liquid phantoms of FIGS. 7a-7c, in accordance with at least one embodiment. The results shown in FIGS. 7a-7f indicate that the increase of repetition numbers may lead to the decreased spread of the feature space projection of both solid and liquid phantoms, hence better separation of flow from static signals in the feature space. Thus, the increase of repetition numbers of B-scans during an experiment may improve the results of fsOMAG. However, increasing the number of B-scans taken would increase the imaging time.

III. Example Artifact Reduction Methods

In a recent study, a weighting factor was applied to a flow signal to suppress artifacts in an image, aiding in image enhancement.

In the study, a spectral domain OCT system with a 68 kHz A-line acquisition speed and a central wavelength of 842 nm was used for retinal scanning of a human eye. To enable OMAG, a repeated B-scan protocol was adopted, wherein B-scan were repeated four times at each slow scan position to extract a flow signal. The time duration for an entire 3D cube scan was about 3.5 seconds.

To scan the phantom sample, a 92 kHz spectral domain OCT system with a central wavelength of 1340 nm was employed with the same scanning protocols as with the human imaging protocol.

Before applying algorithms for OCT angiography, large bulk motion between two repeated B-scans at each position was removed by a block matching method using cross-correlation as a searching criterion, or a phase compensation algorithm if a complex signal is used. An OMAG algorithm based on the complex or intensity signal differentiation can be used to extract the blood flow signal. The equation used was intensity-based, and is provided as follows:

$$F_{OMAG}(x, z) = \frac{1}{R-1} \sum_{i=1}^{R-1} | I_{i+1}(x, z) - I_i(x, z) | \quad [4]$$

Where I is the OCT intensity signal, R is the number of repeated B-scans at each position (R=4), i indicates the $i^{th}$ repeated B-scan and (x,z) is the coordinate in the fast scanning direction (the specific A-line in a B-mode image) and the depth direction, respectively. The calculated flow signal was then log-compressed with a threshold, e.g., 3 dB above noise floor, for image display.

To mitigate or suppress artifacts from highly reflecting structures, a weighted algorithm was applied. The original OMAG flow signal was multiplied by a weighting factor that uses a motion index (MI) as the control variable, as follows:

$$F_{wOMAG}(x,z) = F_{OMAG}(x,z) f(MI(x,z)) \quad [5]$$

where the weighting factor f is a monotonic function of the MI. In this study, the inter-frame pixel decorrelation coefficient (DCC) was used as the MI to scale the OMAG flow signals:

$$MI(x, z) = D(x, z) = \frac{1}{R-1} \sum_{i=1}^{R-1} \frac{(I_{i+1}(x, z) - I_i(x, z))^2}{I_{i+1}^2(x, z) - I_i^2(x, z)} \quad [6]$$

where D is the decorrelation coefficient. The principle for using the decorrelation coefficient is that the OCT signal decorrelates over time and the decorrelation is larger with fast flow than with slow flow. For the scaling factor, different forms of functions may be selected with respect to the independent variable, such as exponential, power or sinusoidal functions. For the current study, the function was set as follows:

$$f(D) = \left(\frac{D}{D_0}\right)^n \quad [7]$$

where D is the DCC for each pixel and $D_0$ is a threshold value for scaling. A threshold of $D_0=1$, n=1 was used to generate the wOMAG retinal images in order to maximally preserve the visibility and connectivity (smoothness) of capillaries but reject the false signals due to hyper-reflective static tissues. The effects of different $D_0$ (0.05, 0.1, 0.2, 0.4) at a fixed n=1, and of different n (0.5, 1, 2, 3) at a fixed $D_0=0.1$ on the quality of vascular image were also evaluated.

OCT angiographic images of the retinal vasculature were also computed using existing algorithms for comparison. The first such algorithm that was used for comparison (CA1) calculates the variance based on the log-compressed intensity signal (LI=log I, where I is the intensity signal as defined in Equation 4). The logarithmic operation turns a multiplicative noise into an additive noise so it is less sensitive to the intensity-induced artifacts:

$$F_{CA1}(x, z) = \frac{1}{R} \sum_{i=1}^{R-1} \left| (LI_i(x, z) - \overline{LI}(x, z))^2 \right| \quad [8]$$

where $\overline{LI}(x,z)$ is the average log-compressed intensity for the four repeated measurements at the same point (x,z). The second algorithm used (CA2) is the decorrelation method and it uses DCC (Equation 6) as the parameter to generate the vascular image. To avoid inaccurate estimation due to a noisy background, a mask based on intensity thresholding was used to display the final image for both the CA1 and the CA2 methods.

An agar phantom was generated to test the effectiveness of the CA2 method in suppressing the artifacts caused by hyper-reflection. Milk drops were added in 2% agar solution during the preparation process to increase its optical scattering. An aluminum wire with a diameter of 1.2 mm was embedded in the phantom to simulate the hyper-reflective feature and its effect on blood flow detection. Because the phantom contained no moving parts, the ideal OMAG image of the phantom should be black, i.e., no flow signal. For OCT imaging, one cross-section was scanned. Each B-scan consisted of 256 A-lines corresponding to a scan range of 1.5 mm.

Additionally, data was obtained from the left eye of a first human subject with DR and the left eye of a second human subject with polypoidal choroidal vasculopathy (PCV). For the DR subject, the macular region of 3 mm×3 mm around the fovea was scanned and for the PCV patient, a temporal peripapillary region of 2.4 mm×2.4 mm was scanned. Enface projection image was used to display the vascular networks located at different retinal layers. The retina was segmented into three layers: the inner retina from ganglion cell layer (GCL) to inner plexiform layer (IPL), the middle retina from inner nuclear layer (INL) to outer plexiform layer (OPL) and the outer retina from outer nuclear layer (ONL) to external limiting membrane (ELM).

Figure 8B:
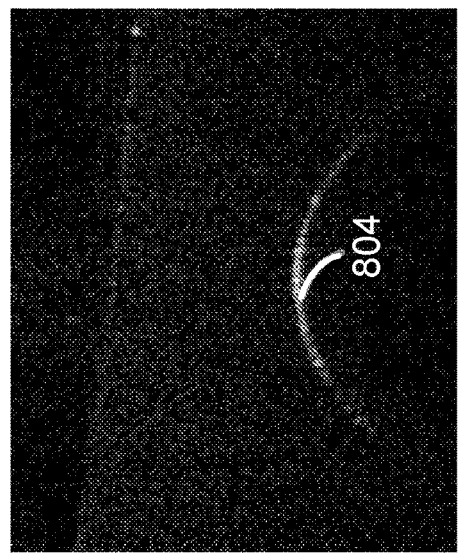
FIG. 8b depicts a flow image of the phantom of FIG. 8a after data processing using an intensity-based OMAG algorithm, in accordance with at least one embodiment.
Figure 8A:
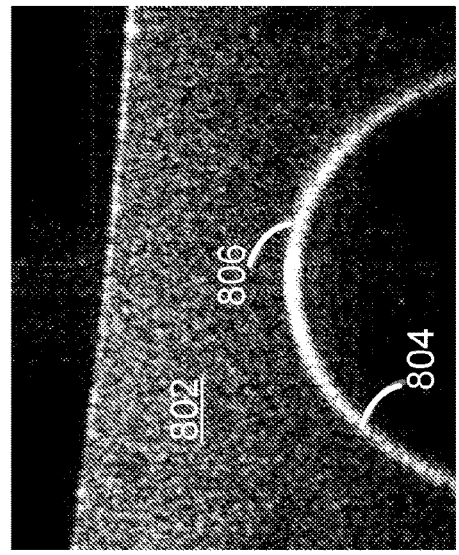
FIG. 8a depicts a structural image of a phantom comprising an embedded aluminum wire, in accordance with at least one embodiment.

FIG. 8a depicts a structural image 800 from an agar phantom comprising an embedded aluminum wire, in accordance with at least one embodiment. The phantom was prepared as discussed above, comprising an agar solution 802 and a wire 804. In FIG. 8a, a hyper-reflective agar-wire interface 806 is clearly observed.

FIG. 8b depicts a flow image 810 after data processing using an intensity-based OMAG algorithm, in accordance with at least one embodiment. In the flow image 810, the hyper-reflective artifacts still appear from the strong reflection from the agar-wire interface.

FIG. 8c depicts a flow image 820 after data processing using wOMAG, in accordance with at least one embodiment. The dataset processed using wOMAG resulted in artifacts being suppressed by about 26 dB and showing in image 820 as being completely removed.

For the DR patient study, two typical B frames that contain hyper-reflective foci were selected to demonstrate how the methods work. The results are shown in FIGS. 9a-j. FIG. 9a depicts an OCT structural projection image 900 of retinal tissue between the ganglion cell layer and the external limiting membrane, in accordance with at least one embodiment. FIG. 9b depicts an OCT structural projection image 910 of the posterior eye, including the choroid in the DR subject, in accordance with at least one embodiment. FIG. 9c depicts an image 920 for detecting blood flow in a B-scan at Line 1 from FIG. 9a, which was obtained using a traditional OMAG method, in accordance with at least one embodiment. FIG. 9d depicts an image 930 for detecting blood flow in a B-scan at Line 2 from FIG. 9a, using a traditional OMAG method, in accordance with at least one embodiment. FIG. 9e depicts an image 940 for detecting blood flow in a B-scan at Line 1 from FIG. 9a, which was obtained using the wOMAG method discussed above, in accordance with at least one embodiment. FIG. 9f depicts an image 950 for detecting blood flow in a B-scan at Line 2 from FIG. 9a, which was obtained using the wOMAG method, in accordance with at least one embodiment. FIG. 9g depicts an image 960 for detecting blood flow in a B-scan at Line 1 from FIG. 9a, which was obtained using the CA1 method discussed above, in accordance with at least one embodiment. FIG. 9h depicts an image 970 for detecting blood flow in a B-scan at Line 2 from FIG. 9a, which was obtained using the CA1 method, in accordance with at least one embodiment. FIG. 9i depicts an image 980 for detecting blood flow in a B-scan at Line 1 from FIG. 9a, which was obtained using the CA2 method discussed above, in accordance with at least one embodiment. FIG. 9j depicts an image 990 for detecting blood flow in a B-scan at Line 2 from FIG. 9a, which was obtained using the CA2 method, in accordance with at least one embodiment.

From FIGS. 9c and 9d, it can be seen that OMAG is very sensitive to the flow signal, but the hyper-reflective foci also show up on the images 920 and 930, which are regarded as artifacts when performing vascular detection.

The wOMAG method effectively suppresses these artifacts, as shown in FIGS. 9e-9f. The CA1 and CA2 methods also suppress hyper-reflection artifacts well and perform similarly with each other for the typical B-frames shown in FIG. 9g-9j. However, the images obtained using the CA1 and CA2 methods over-suppress the flow information, in particular the capillaries in the deep retinal layer, when compared with OMAG results. The wOMAG method works well to provide a better balance between the sensitive detection of capillary network and the suppression of hyper-reflective artifacts.

FIG. 10a depicts an image 1000 illustrating segmentation of the three retinal layers, in accordance with at least one embodiment. The inner retinal layer 1002, the middle retinal layer 1004, and the outer retinal layer 1006 are shown in image 1000. FIG. 10b depicts an enlarged view 1050 of a portion of the image 1000 of FIG. 10a, in accordance with at least one embodiment.

FIG. 10c depicts an en face vascular image series 1060 of the different layers using an OMAG method, in accordance with at least one embodiment.

FIG. 10d depicts an en face vascular image series 1070 of the different layers using the wOMAG method discussed above, in accordance with at least one embodiment.

FIG. 10e depicts an en face vascular image series 1080 of the different layers using the CA1 method, in accordance with at least one embodiment.

FIG. 10f depicts an en face vascular image series 1090 of the different layers using the CA2 method, in accordance with at least one embodiment.

In each of FIGS. 10c-10f, for the image series 1060, 1070, 1080, and 1090, the first image is marked as "1" representing the inner retinal layer, the second image in the series is marked as "2" representing the middle retinal layer, the third image in the series is marked as "3" representing the outer retinal layer, and the fourth image in the series is marked as "4" representing the total retina.

In image 4 of the image series 1070 of FIG. 10d, the white circle 1072 shows the region where capillaries can be seen more clearly from use of the wOMAG method than for the Figures showing the other methods. CA1 and CA2 performed comparably with each other and both methods can be used to suppress the hyper-reflective artifacts as well. However, the continuity and smoothness of the vasculature are compromised in CA1 and CA2 compared to that of OMAG and wOMAG. The degradation of vascular image quality in CA1 and CA2 is especially observed in the middle retinal layer, as shown in the second images, images 2, in image series 1080 and 1090, where most of the blood vessels are capillaries that are more vulnerable to pathological attack.

Figure 11B:
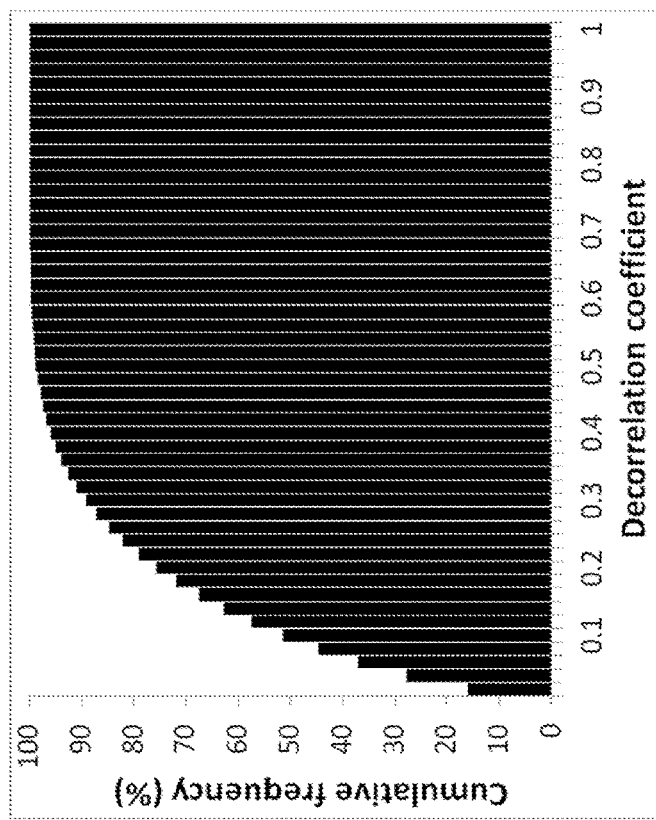
FIG. 11b depicts a cumulative histogram of the decorrelation coefficients in the scanned volume of FIG. 10a, in accordance with at least one embodiment.
Figure 11A:
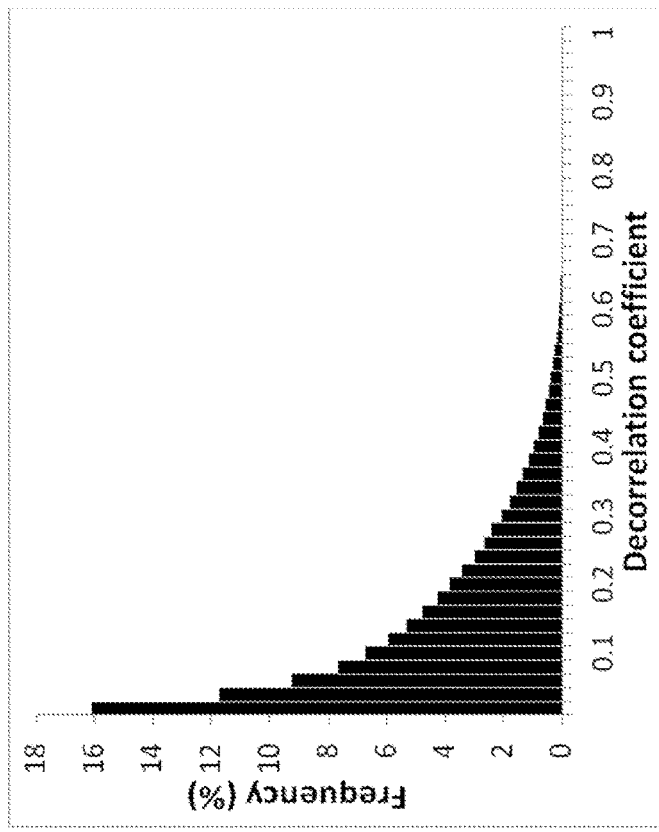
FIG. 11a depicts a frequency histogram of the decorrelation coefficients in the scanned volume of FIG. 10a, in accordance with at least one embodiment.

FIG. 11a depicts a frequency histogram 1100 of the decorrelation coefficients in the scanned volume of FIG. 10a, in accordance with at least one embodiment. In FIG. 11a, percent frequency is plotted over the decorrelation coefficient. FIG. 11a depicts the overall distribution of the speckle DCC for all the pixels in the scanned volume. From FIG. 11a, a monotonically decreasing trend of frequency for the DCC is observed, and 50% of the coefficients lie below 0.1, which indicates the static part of the issue. As shown in FIG. 11a, there is no clear cutoff value of DCC that can be used as a threshold to separate the static tissue from the blood vessels. Thus, a further study was conducted to show how the threshold $D_0$ and n in the weighting factor of Equation 7 affect the results.

FIG. 11b depicts a cumulative histogram 1150 of the decorrelation coefficients in the scanned volume of FIG. 10a, in accordance with at least one embodiment. In FIG. 11b, the percent cumulative frequency is plotted over the decorrelation coefficient.

Figure 12:
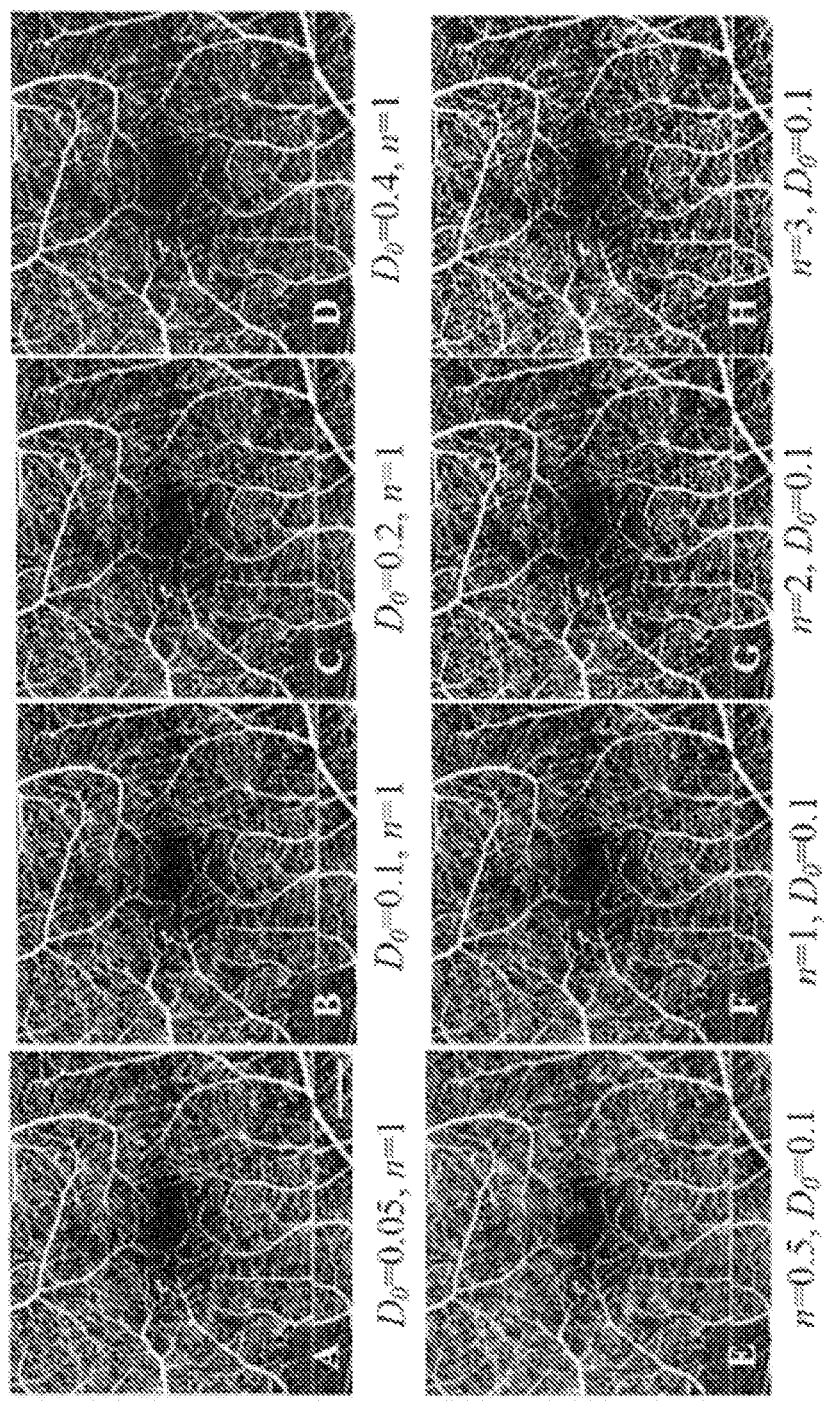
FIG. 12 depicts an en face vascular image series of a retina, in accordance with an example embodiment.

FIG. 12 depicts an en face vascular image series 1200 of the whole retina, in accordance with an example embodiment. The image series 1200 shows $D_0$ changing at four values: 0.05, 0.1, 0.2, and 0.4, while n=1, and then n changing at four values: 0.5, 1, 2, and 3, while $D_0$=0.1. As shown in the image series 1200, the results of wOMAG are almost the same when $D_0$ changes with a fixed n. When n increases, there is a better suppression of the hyper-reflection and the blood vessels become brighter with an increased image contrast; however, there is a loss of smoothness and connectivity of the small blood vessels. It was found to be preferable to set n=about 1 to 2 to obtain results with satisfactory artifact suppression.

As demonstrated by the results discussed above, the weighting method effectively suppresses hyper-reflective static tissues in scanned images. There are numerous applications for suppression of hyper-reflective static tissues, as such tissues are commonly found in patients with pathologies such as DR, AMD, and PCV, among others.

Figure 13:
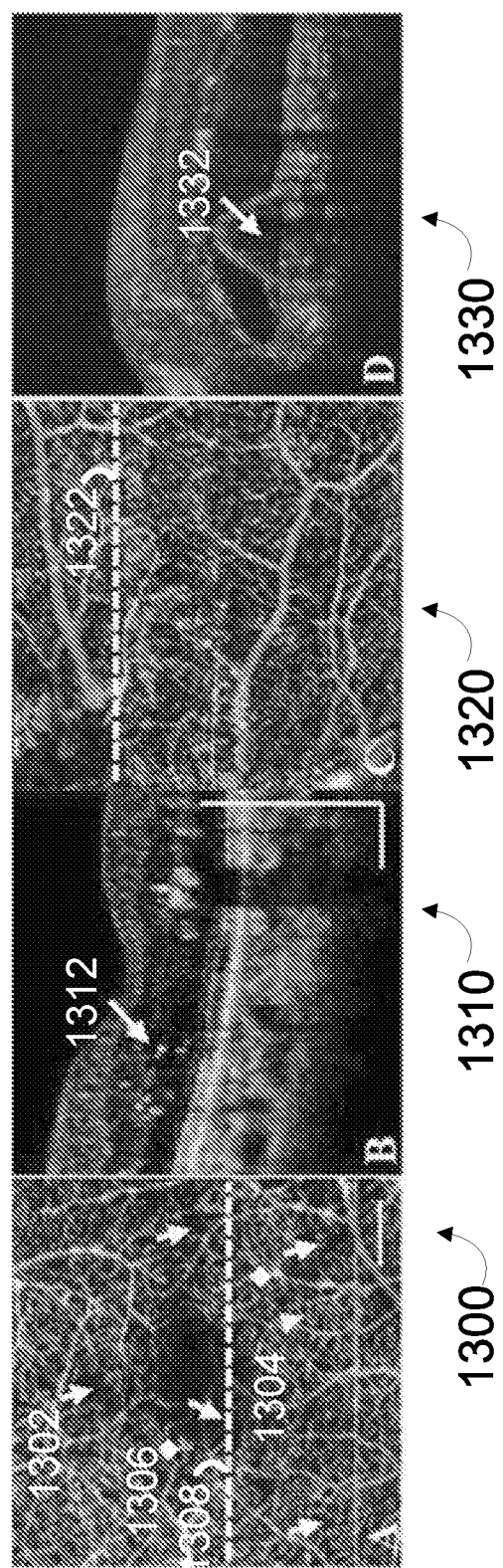
FIG. 13 depicts images of example in vivo applications of the methods of FIG. 2 and Equations 4-8, in one example embodiment.

FIG. 13 depicts images 1300, 1310, 1320, and 1330 of example in vivo applications of the methods discussed with respect to FIG. 2 and Equations 4-8, in one example embodiment. Due to the ability of wOMAG to suppress artifacts induced by hyper-reflection, the vascular network can be seen more clearly for in vivo samples.

Image 1300 depicts the left eye in a patient with DR, showing pathologies including capillary drop-out via arrows 1302, tortuosity via arrowhead 1304, and possible microaneurysm via diamonds 1306.

Image 1310 depicts a structural OCT image scanned from the dotted line 1308 in image 1300. Image 1310 shows the coexistence of an edema 1312 with significant capillary drop-out.

Image 1320 depicts a weighted wOMAG image of the left eye in a patient with PCV. Image 1330 depicts a structural OCT image scanned at the dotted line 1322 showing the existence of a pigment epithelial detachment 1332 below the hyper-reflective foci. Using structural OCT images to locate pathologies such as those shown in images 1310 and 1330 may be helpful in a comprehensive diagnosis of the disease severity when combined with vascular images from wOMAG.

In addition to aiding in the investigation of ocular pathologies, the proposed wOMAG methodology may also be useful in observing normal retina, where the reflection of specific layers is strong, including the NFL and the RPE. For the RPE layer, the suppression of artifacts may be useful for studying the choroidal vasculature, especially the choriocapillaris that is just beneath the RPE, which is otherwise inseparable without the suppression of hyper-reflective RPE.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A method comprising:
    acquiring a flow image from a plurality of first optical microangiography (OMAG) scans of a sample, wherein the sample comprises a biological tissue having fluid flow therethrough, the flow image comprising a first plurality of pixels;
    acquiring a structure image from a second OMAG scan of the sample, the structure image comprising a second plurality of pixels;
    comparing first intensities of the first plurality of pixels respectively to second intensities of the second plurality of pixels;
    differentiating the first plurality of pixels, using results of the comparing, into a first data group representing static structure signals and a second data group representing flow signals; and
    suppressing the first data group in the flow image.

2. The method of claim 1, further comprising:
    acquiring a phantom flow image from a plurality of third OMAG scans of a fluid phantom;
    acquiring a phantom structure image from a fourth OMAG scan of a solid phantom;
    plotting, onto a graph, data based on pixel intensity values from the phantom flow image and pixel intensity values from the phantom structure image;
    calculating a probability distribution of data designating flow signals and data designating structure signals from the pixel intensity values from the phantom flow image and the pixel intensity values from the phantom structure image; and
    mapping the probability distribution of data onto the graph.

3. The method of claim 2, further comprising:
    setting pixels with a probability greater than a threshold to zero intensity on the flow image.

4. The method of claim 1, wherein plotting data based on pixel intensity values from the flow image and pixel intensity values from the structure image comprises plotting a logarithm of structural pixel intensity over a ratio of flow pixel intensity to structural pixel intensity.

5. The method of claim 1, wherein plotting data based on pixel intensity values from the flow image and pixel intensity values from the structure image comprises plotting data having pixel intensity values above a noise level.

6. The method of claim 2, wherein the graph is one of a two-dimensional (2D) graph or a three-dimensional (3D) graph.

7. The method of claim 2, wherein differentiating the data by location on the graph further comprises determining a boundary on the graph between the first data group and the second data group.

8. The method of claim 1, wherein the fluid flow is a blood flow, and wherein the method further comprises quantifying blood perfusion within the biological tissue.

9. The method of claim 1, wherein acquiring the flow image from the plurality of OMAG scans of the sample comprises generating the flow image from a plurality of repeated B-scans of the sample.

10. The method of claim 1, wherein the sample comprises one of the following: a brain, an eye, a retina, a tumor, a heart, skin, a kidney, a gastroenterology tract, a productive system, and a cochlear.

11. The method of claim 10, wherein the method is used in imaging cerebrovascular perfusion, retinal microcirculation, tumor progression, posterior eye vascular imaging, or angiography.

12. The method of claim 1, wherein differentiating the first plurality of pixels comprises differentiating the first plurality of pixels additionally using logarithms of the second intensities of the second plurality of pixels.

13. The method of claim 1, wherein differentiating the first plurality of pixels comprises using a Gaussian process classification.

14. A method comprising:
    extracting a flow signal from a plurality of optical microangiography (OMAG) scans of a sample, wherein the sample comprises a biological tissue having fluid flow therethrough;
    generating a weighting factor by normalizing and inverting a structure image of the sample;
    producing a weighted flow signal by multiplying the flow signal by the weighting factor; and
    displaying an image of the sample from the weighted flow signal.

15. The method of claim 14, wherein the weighting factor comprises a motion index that is an inter-frame pixel decorrelation coefficient.

16. The method of claim 14, wherein the plurality of OMAG scans of the sample comprises a plurality of adjacent B-scans of the sample.

17. The method of claim 14, further comprising:
    compressing the weighted flow signal with a threshold.

18. A system for in vivo imaging, comprising:
    an optical micro-angiography (OMAG) apparatus configured to generate images from living tissue; and
    a non-transitory computer-readable medium having stored therein instructions executable to cause a computing device to carry out the method of claim 1.

* * * * *